United States Patent
Yi et al.

(10) Patent No.: US 10,503,306 B2
(45) Date of Patent: Dec. 10, 2019

(54) PRESSURE SENSOR COMPRISING LAYER OF DISCONTINUOUS CONDUCTIVE PATTERNS, DEVICE COMPRISING THE SAME, AND APPARATUS AND METHOD FOR DETECTING PRESSURE

(71) Applicant: KOREA INSTITUTE OF SCIENCE AND TECHNOLOGY, Seoul (KR)

(72) Inventors: Hyunjung Yi, Seoul (KR); Sungwoong Kim, Seoul (KR); Seungwoo Lee, Seoul (KR); Ki-Young Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/722,266

(22) Filed: Oct. 2, 2017

(65) Prior Publication Data

US 2018/0095580 A1   Apr. 5, 2018

(30) Foreign Application Priority Data

Sep. 30, 2016   (KR) .......................... 10-2016-0127141

(51) Int. Cl.
*G06F 3/045*   (2006.01)
*G06F 3/041*   (2006.01)
*G06F 3/044*   (2006.01)
*G01L 1/20*   (2006.01)
(Continued)

(52) U.S. Cl.
CPC ........ *G06F 3/0414* (2013.01); *A61B 5/02444* (2013.01); *G01L 1/205* (2013.01); *G06F 3/044* (2013.01); *G06F 3/045* (2013.01); *A61B 5/0215* (2013.01); *A61B 2562/0247* (2013.01); *A61B 2562/046* (2013.01)

(58) Field of Classification Search
USPC .................................. 345/173, 174, 204, 205
See application file for complete search history.

(56) References Cited

U.S. PATENT DOCUMENTS 7,464,613 B2   12/2008   Bieck et al.
9,360,971 B2   6/2016   Barton et al.
10,017,537 B2   7/2018   Yi et al.
(Continued)

FOREIGN PATENT DOCUMENTS

KR   1020050084524 A   8/2005
KR   1020100004324 A   1/2010
(Continued)

OTHER PUBLICATIONS

He Tian et al., "A graphene-based resistive pressure sensor with record-high sensitivity in a wide pressure range," Scientific Reports, Feb. 27, 2015, pp. 1-6.
(Continued)

*Primary Examiner* — Thuy N Pardo
(74) *Attorney, Agent, or Firm* — Cantor Colburn LLP

(57) ABSTRACT

Provided is a pressure sensor including: a first layer having first conductivity and at least one conductive region; a second layer contacting the first layer to be disposed thereon and having second conductivity; and a plurality of terminals that are electrically connected with the second layer and spaced apart from the at least one conductive region, wherein the at least one conductive region has electrical conductivity that is greater than or equal to that of the second layer.

33 Claims, 12 Drawing Sheets

Specification includes a Sequence Listing.

(51) Int. Cl.
  *A61B 5/024* (2006.01)
  *A61B 5/0215* (2006.01)

(56) References Cited

U.S. PATENT DOCUMENTS

| | | | | |
|---|---|---|---|---|
| 2002/0149572 A1* | 10/2002 | Schulz | .................... | G06F 3/044 |
| | | | | 345/174 |
| 2010/0242629 A1 | 9/2010 | Leuenberger et al. | | |
| 2012/0256865 A1* | 10/2012 | Hashimoto | ............. | G06F 3/041 |
| | | | | 345/173 |
| 2012/0327023 A1* | 12/2012 | Hashimoto | ............. | G06F 3/041 |
| | | | | 345/174 |
| 2013/0063387 A1* | 3/2013 | Takai | .................... | G06F 3/0414 |
| | | | | 345/173 |
| 2013/0118773 A1* | 5/2013 | Liu | ........................... | C09J 9/02 |
| | | | | 174/117 F |
| 2014/0218334 A1* | 8/2014 | Shibata | .................... | G06F 3/044 |
| | | | | 345/174 |
| 2016/0004358 A1* | 1/2016 | Frey | ........................ | G06F 3/044 |
| | | | | 345/174 |
| 2016/0378260 A1* | 12/2016 | Weaver | .................... | G06F 3/041 |
| | | | | 345/174 |
| 2017/0009105 A1* | 1/2017 | Baetzold | ............ | B32B 37/1284 |
| | | | | 345/174 |

FOREIGN PATENT DOCUMENTS

| | | |
|---|---|---|
| KR | 1020140124067 A | 10/2014 |
| KR | 1020140129134 A | 11/2014 |

OTHER PUBLICATIONS

Korean Office Action for corresponding Korean Patent Application No. 10-2016-0127141 dated Jul. 19, 2018.

\* cited by examiner

PRESSURE SENSOR COMPRISING LAYER OF DISCONTINUOUS CONDUCTIVE PATTERNS, DEVICE COMPRISING THE SAME, AND APPARATUS AND METHOD FOR DETECTING PRESSURE

CROSS-REFERENCE TO RELATED APPLICATION

This application claims the benefit of Korean Patent Application No. 10-2016-0127141, filed on Sep. 30, 2016, in the Korean Intellectual Property Office, the disclosure of which is incorporated herein in its entirety by reference.

BACKGROUND

1. Field

One or more embodiments relate to a pressure sensor with a discontinuous conductive pattern, a device including the same, a pressure sensitive apparatus including the pressure sensor, and a method of sensing pressure.

2. Description of the Related Art

Recently, commercialization and popularization of portable devices or display devices configured with a touch user interface results in widening of the range of pressure sensor applications. Such a touch-pressure sensor has attracted attention as a technology that can be applied not only to electronic devices, but also to robot development that can measure and respond to external environment and stimulus. Due to the increased interest in the Ubiquitous Environment and the development of humanoid robot technology, there is an increasing interest in a robot that spontaneously responds to and copes with complicated and fluid environments or external stimuli, beyond a simple robot that receives one-dimensional commands and executes the commands repeatedly. In order for such a robot to spontaneously respond to external stimuli or environmental changes, a tactile pressure sensing system counted on a robot surface should convert external stimuli or environmental changes into electrical signals so that the robot can respond spontaneously and/or flexibly with the user's commands.

In addition, a pressure sensor based on a flexible device is applicable not only to emotional electronic devices and humanoid robots, but also to sensory systems that manage physical activities and regular sports activities. For example, an ultra-sensitive pressure sensor based on a flexible device can be used for measuring heart pulse saves through human skin, or can be attached to shoe soles to work as a wearable sensor system for collecting data regarding walking or habits of a user. To construct such a wearable sensor system, the development of a sensor which is excellent in bending and restoring of a sensor's basic unit and has excellent mechanical flexibility and stability is required.

A conventional pressure sensor has been implemented by using characteristics of a piezo-resistive material having pressure-dependent resistance, or characteristics that the resistance changes when the shape of a complicated structure of the sensor changes according to the pressure applied thereto. In this regard, a complicated manufacturing process is required for a material having pressure-dependent resistance or for a complicated structure of the sensor, and accordingly, there may be a limit to the diversity and applicability of the material selection.

Therefore, it is required to realize a high-performance pressure sensor by a simple process using a typical conductive material.

SUMMARY

One or more embodiments include a pressure sensor including:
a first layer comprising at least one conductive region having first electrical conductivity;
a second layer contacting the first layer to be disposed thereon and having second electrical conductivity; and
a plurality of terminals electrically connected to the second layer and spaced apart from the at least one conductive region,
wherein electrical conductivity of the at least one conductive region is the same as or greater than that of the second layer.

In some embodiments, resistance of the first layer (first layer resistance, $R_1$), resistance of the second layer (second layer resistance, $R_2$), and resistance between the first layer and the second layer (contact resistance, $R_{1-2}$) has a relationship of $R_1 \leq R_2 < R_{1-2}$ before application of external pressure In some embodiments, an electric current changes depending on application of pressure.

In some embodiments, the at least one conductive region has a discontinuous pattern.

In some embodiments, the at least one conductive region has a line pattern disposed discontinuously in one direction or an island-type pattern disposed discontinuously in a plurality of directions.

In some embodiments, the discontinuous pattern has a rectangular, triangular, polygonal, circular, elliptical, stripe, or irregular shape, or a combination thereof.

In some embodiments, the discontinuous pattern has the same or different electrical conductivity.

In some embodiments, the first layer is disposed on a first substrate, and
the sum of areas of the at least one conductive region is in a range of about 25% to about 95% based on the total area of the first substrate.

In some embodiments, the first layer and the second layer each independently comprises at least one selected from gold (Au), silver (Ag), copper (Cu), aluminum (Al), platinum (Pt), zinc (Zn), nickel (Ni), an alloy or composite thereof, a conductive polymer, a conductive fiber, and a graphitic material.

In some embodiments, the graphitic material is at least one selected from a graphene sheet, a highly oriented pyrolytic graphite (HOPG) sheet, a graphene oxide sheet, a reduced graphene oxide sheet, a single-walled carbon nanotube, a double-walled carbon nanotube, a multi-walled carbon nanotube, fullerene, and a composite thereof.

In some embodiments, the second layer comprises the graphitic material, and further comprises a phage binding to the graphitic material, wherein the phage binding is between the graphitic material and a peptide displayed on a coat protein of the phage or a fragment thereof.

In some embodiments, the second layer comprises the graphitic material and a peptide binding to the graphitic material.

In some embodiments, an internal structure of the second layer is a network structure.

In some embodiments, the network structure further comprises a nanoparticle.

In some embodiments, the pressure sensor further comprises:
- a first substrate disposed on the first layer; and
- a second substrate disposed on a surface of the second layer not facing the first substrate.

In some embodiments, at least one of the first substrate and the second substrate has an uneven structure including a convex portion, a concave portion, or a combination thereof.

In some embodiments, a cross section of the convex portion or the concave portion has a triangular, square, polygonal, circular, oval, or irregular shape.

In some embodiments, the first substrate, the second substrate, or both first and second substrates are each a flexible substrate.

One or more embodiments include a device including the pressure sensor.

One or more embodiments include a mapping method of determining an intensity and a position of pressure applied to the pressure sensor by using the pressure sensor.

One or more embodiments include a method of manufacturing the pressure sensor.

One or more embodiments include a pressure-sensing apparatus and a method capable of accurately detect the intensity of pressure, and furthermore capable of detecting both an intensity and a position of pressure applied to the pressure-sensing apparatus.

Additional aspects will be set forth in part in the description which follows and, in part, will be apparent from the description, or may be learned by practice of the presented embodiments.

According to one or more embodiments, a pressure sensor includes:
- a first layer including at least one conductive region having first electrical conductivity;
- a second layer contacting the first layer to be disposed thereon and having second electrical conductivity; and
- a plurality of terminals electrically connected to the second layer and spaced apart from the at least one conductive region,
- wherein electrical conductivity of the at least one conductive region is the same as or greater than that of the second layer.

According to one or more embodiments, a device includes the pressure sensor.

According to one or more embodiments a method of manufacturing the pressure sensor includes:
(a) a process of manufacturing a second layer by manufacturing a material having electrical conductivity in the form of a film;
(b) a process of manufacturing a first layer including at least one conductive region including a material having the same or higher electrical conductivity than that of the material included in the second layer;
(c) a process of disposing the first layer on a first substrate such that the at least one conductive region is disposed toward a surface opposite to the first substrate;
(d) a process of disposing the second layer on the first layer such that the second layer faces the at least one conductive region of the first layer; and
(e) a process of disposing a plurality of terminals on one of the first and second layers such that the plurality of terminals are spaced apart from the at least one conductive region and electrically connected to the second layer.

According to one or more embodiments, a method of sensing pressure by using a pressure sensor, which includes a first layer having first electrical conductivity, a second layer having second electrical conductivity, and a plurality of terminals electrically connected to the second layer, includes:
- measuring initial resistance between each of the plurality of terminals;
- detecting a changed resistance value between each of the plurality of terminals; and
- determining a pressure intensity based on the changed resistance value between each of the plurality of terminals.

In some embodiments, the first layer comprises at least one conductive region having first electrical conductivity,
- the second layer contacts the first layer to be disposed thereon, and
- the plurality of terminals electrically contact the second layer and are spaced apart from the first layer.

In some embodiments, the first electrical conductivity is the same as or greater than the second electrical conductivity.

In some embodiments, the at least one conductive region comprises a conductive region array of n*m (where n and m are each independently a natural number of 1 or more),
- the plurality of terminals comprise, outside the conductive region array, a plurality of electrodes disposed in a horizontal direction and a plurality of electrodes disposed in a vertical direction, and
- the method further comprises determining a pressure intensity and a pressure position to which the pressure is applied based on the changed resistance value between each of the plurality of terminals.

In some embodiments, the determining of the pressure position comprises determining a pressure position by a combination of terminals whose changed resistance value is greater than a standard resistance value.

In some embodiments, the conductive region array comprises conductive regions having different electrical conductivity each other.

According to one or more embodiments, a pressure-sensing apparatus includes:
- a pressure sensor including a first layer having first electrical conductivity, a second layer having second electrical conductivity, and a plurality of electrodes electrically connected to the second layer;
- a resistance-measuring unit measuring resistance between each of the plurality of terminals; and
- a processing unit measuring initial resistance between each of the plurality of terminals and detecting a changed resistance value between each of the plurality of terminals and determining a pressure intensity based on the changed resistance value between each of the plurality of terminals.

In some embodiments, the first layer comprises at least one conductive region having first electrical conductivity,
- the second layer contacts the first layer to be disposed thereon, and
- the plurality of terminals electrically contact the second layer and spaced apart from the first layer.

In some embodiments, the first electrical conductivity is the same as or greater than the second electrical conductivity.

In some embodiments, the at least one conductive region comprises a conductive region array of n*m (where n and m are each independently a natural number of 1 or more),
- the plurality of terminals comprise, outside the conductive region array, a plurality of electrodes disposed in a horizontal direction and a plurality of electrodes disposed in a vertical direction, and the processing unit determines a pressure intensity and a pressure position to which the pressure is applied, based on a changed resistance value between each of the plurality of electrodes.

In some embodiments, the processing unit determines a pressure position by a combination of terminals whose changed resistance value is greater than a standard resistance value.

In some embodiments, the conductive region array comprises conductive regions having different electrical conductivity each other.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
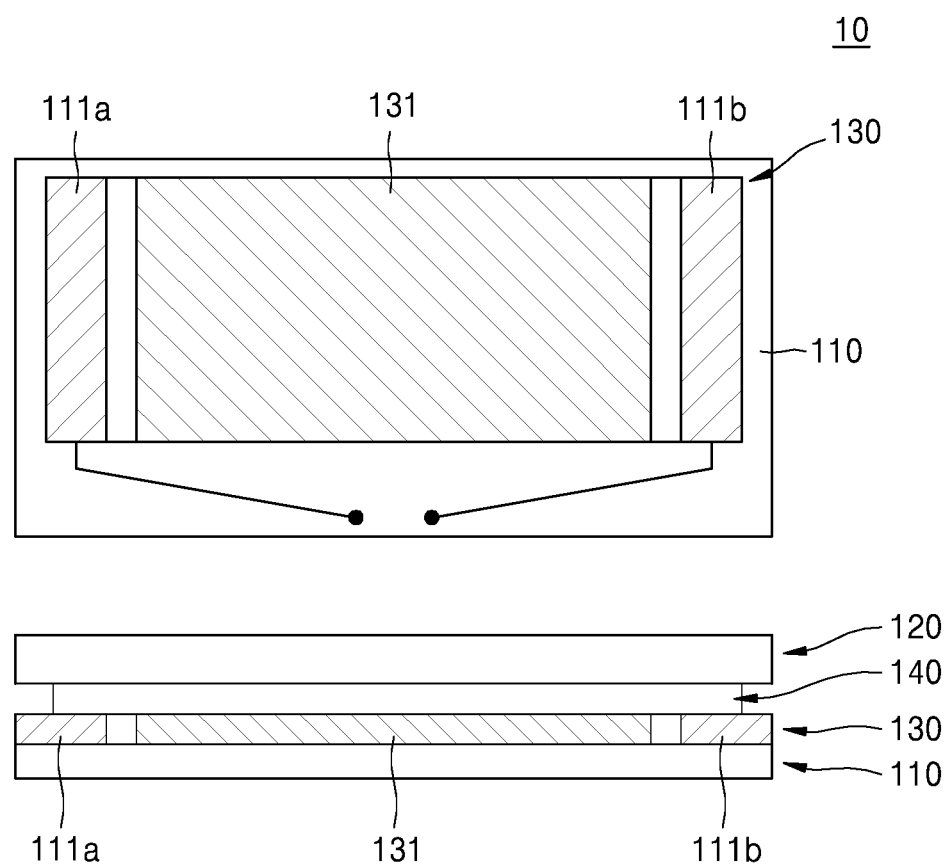
FIG. 1 is a diagram schematically showing a structure of a pressure sensor according to an embodiment.

Reference will now be made in detail to embodiments regarding a pressure sensor, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

According to an aspect of the present disclosure, there is provided a pressure sensor comprising: a first layer comprising at least one conductive region having first electrical conductivity; a second layer contacting the first layer to be disposed thereon and having second electrical conductivity; and a plurality of terminals electrically connected to the second layer and spaced apart from the at least one conductive region, wherein electrical conductivity of the at least one conductive region is the same as or greater than that of the second layer.

Here, the pressure sensor may further include a first substrate on a surface on the first layer, wherein the first layer is disposed on the first substrate.

In one embodiment, the pressure sensor may further include a second substrate on a surface of the second layer, wherein the surface does not face the first substrate.

FIG. 1 is a diagram schematically showing a structure of a pressure sensor according to an embodiment.

In one embodiment, a pressure sensor 10 includes: a first substrate 110; a second layer 140 disposed opposite to the first substrate 110; a first layer 130 disposed on a surface of the first substrate 110, wherein the surface faces the second layer 140, and including at least one conductive region 131; a second substrate 120 disposed on a surface of the second layer 140 not facing the first substrate 110; and at least two terminals 111a and 111b that are electrically connected to the second layer 140 and spaced apart from the at least one conductive region 131, wherein the at least two terminals 111a and 111b are each independently disposed on one of the first layer 130 and the second layer 140, and electrical conductivity of the at least one conductive region 131 is the same as or greater than that of the second layer 140.

For example, the electrical conductivity of the at least one conductive region may be greater than that of the second layer.

The term "pressure sensor" as used herein may be used interchangeably with a term "touch sensor" or "tactile sensor", and may refer to an apparatus, an element, or equipment that is able to sense a given force, contact, pressure, tactus, or touch and then convert it to a signal (for example, an electrical signal). The pressure sensor according to an embodiment may be a flexible pressure sensor or an integrated or miniaturized pressure sensor having a thickness of less than about 1 mm. In addition, the pressure sensor according to an embodiment has excellent electrical characteristics under control, and is excellent in mechanical flexibility and stability, and thus may be used applied to a humanoid-based robot, a touch display, a wearable device for biometric information measurement, a smart vehicle, aviation application, simulation, process control, human-friendly IT, a fingerprint recognition system, or a bio-monitoring smart sensor.

Here, electricity may flow over the conductive region included in the first layer. However, the conductive region is spaced apart from terminals configured for electrical connection, the first layer is not entirely conductive. In addition, the second layer may be a conductive layer.

As described above, when the electrical conductivity of the conductive region included in the first layer is the same as or greater than that of the second layer, the pressure sensor may have increased reactivity and sensitivity compared to a case where the electrical conductivity of the conductive region included in the first layer is not greater than or not the same as that of the second layer. Here, the reactivity of the pressure sensor may refer to a signal change of a device to which pressure is applied. In addition, the sensitivity of the pressure sensor may refer to minimum pressure that the pressure sensor may sense, and increased or high sensitivity may refer to decreased or low sensible pressure. In addition, a driving range of the pressure sensor, which will be described later, may refer to a range of pressure that the pressure sensor may sense, and an increased or wide driving range may refer to an increased or wide range of pressure that the pressure sensor may sense.

For example, the at least two (plurality of) terminals may all be disposed on the first layer, may all be disposed on the second layer, or some of the at least two terminals may be disposed on the first layer while the rest of the at least two terminals may be disposed on the second layer. However, regardless of the structure in which the at least two terminals are disposed, in the pressure sensor according to the present disclosure, the at least two terminals may be spaced apart from the conductive region of the first layer and electrically connected with the second layer. Through the at least terminals, an electrical connection between the outside and the pressure sensor is possible.

In one or more embodiments, at least a portion of the at least two terminals may protrude out of the pressure sensor for easy connection with the outside.

In one or more embodiments, at least one of the at least two terminals may be disposed on each end of the pressure sensor.

For example, at least one of the two terminals may be disposed on each of two ends, which face each other, of the pressure sensor. In one or more embodiments, the at least two terminals may each independently consist of a material that is same as or different from a material constituting the conductive region.

In one or more embodiments, resistance of the first layer (first layer resistance, $R_1$), resistance of the second layer (second layer resistance, $R_2$), and resistance by a contact between the first layer and the second layer (contact resistance, $R_{1\text{-}2}$) has a relationship of $R_1 \leq R_2 < R_{1\text{-}2}$ before application of external pressure. For example, $R_1$, $R_2$, and $R_{1\text{-}2}$ may have a relationship of $R_1 \leq R_2 < R_{1\text{-}2}$ before application of external pressure. For example, $R_1$, $R_2$, and $R_{1\text{-}2}$ may have a relationship of $R_1 R \leq_2 < R_{1\text{-}2}$ before application of external pressure and $R_{1\text{-}2}$ becomes lower and may have a relationship of $R_{1\text{-}2} < R_1 \leq R_2$ after application of external pressure. Such a change in the relationship is caused by which the contact resistance $R_{1\text{-}2}$ changes with the application of external pressure. According to such a change in $R_{1\text{-}2}$ or in the relationship with the application of external pressure, the flow of current in a device is changed, and consequently, the overall resistance of the device is also changed. Here, the degree to which the current flow changes is determined depending on the absolute magnitude of $R_1$, $R_2$, and $R_{1\text{-}2}$.

In one or more embodiments, the pressure sensor may change the flow of current as pressure is applied thereto.

Here, the term "flow of current" as used herein refers to a path or direction through which current flows in the pressure sensor.

Figure 2:
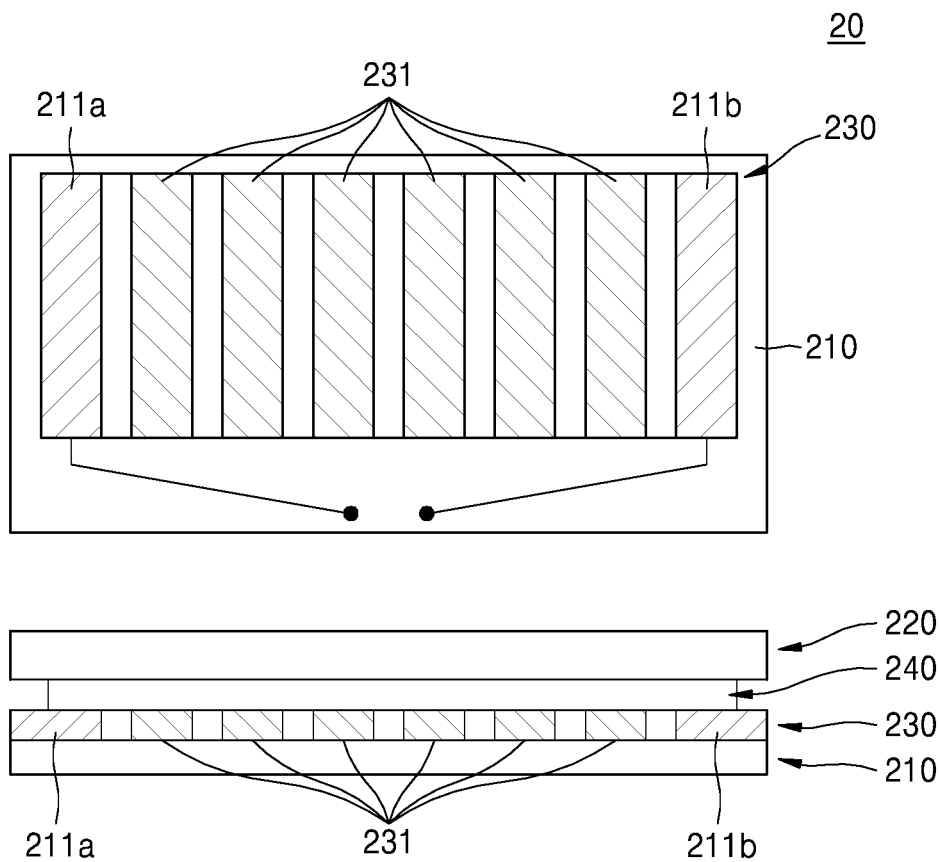
FIG. 2 is a diagram schematically showing a structure of a pressure sensor according to another embodiment.

FIG. 2 is a diagram schematically showing a structure of a pressure sensor according to another embodiment.

In an embodiment, a pressure sensor 20 includes: a first substrate 210; a second layer 240 disposed opposite to the first substrate 210; a first layer 230 disposed on a surface of the first substrate 210, wherein the surface faces the second layer 230, and including at least one conductive region 231 having a discontinuous pattern; a second substrate 220 disposed on a surface of the second layer 240, wherein the surface does not face the first substrate 210; and two or more terminals 211a and 211b electrically connected to the second layer 240 and spaced apart from the conductive region 231, wherein electrical conductivity of the conductive region 231 having discontinuous pattern is the same as or greater than that of the second layer 240.

Figure 3:
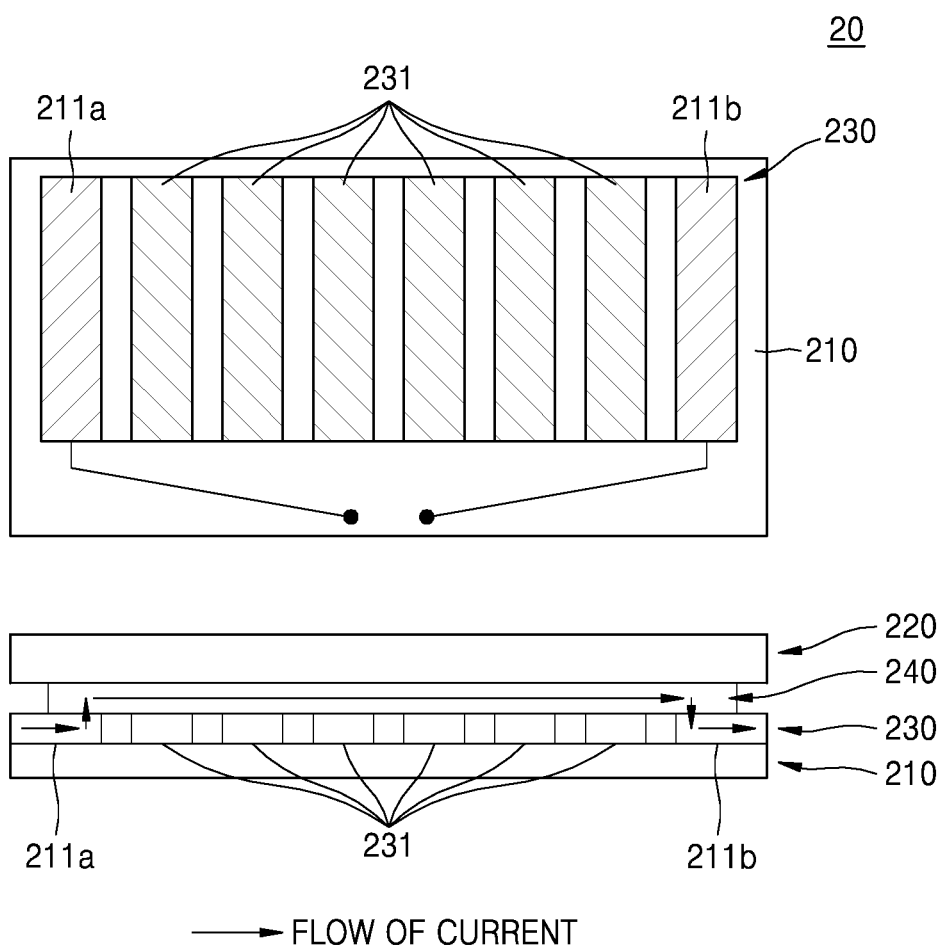
FIG. 3 is a diagram schematically showing the flow of current in a device before applying pressure to the pressure sensor of FIG. 2.
Figure 4:
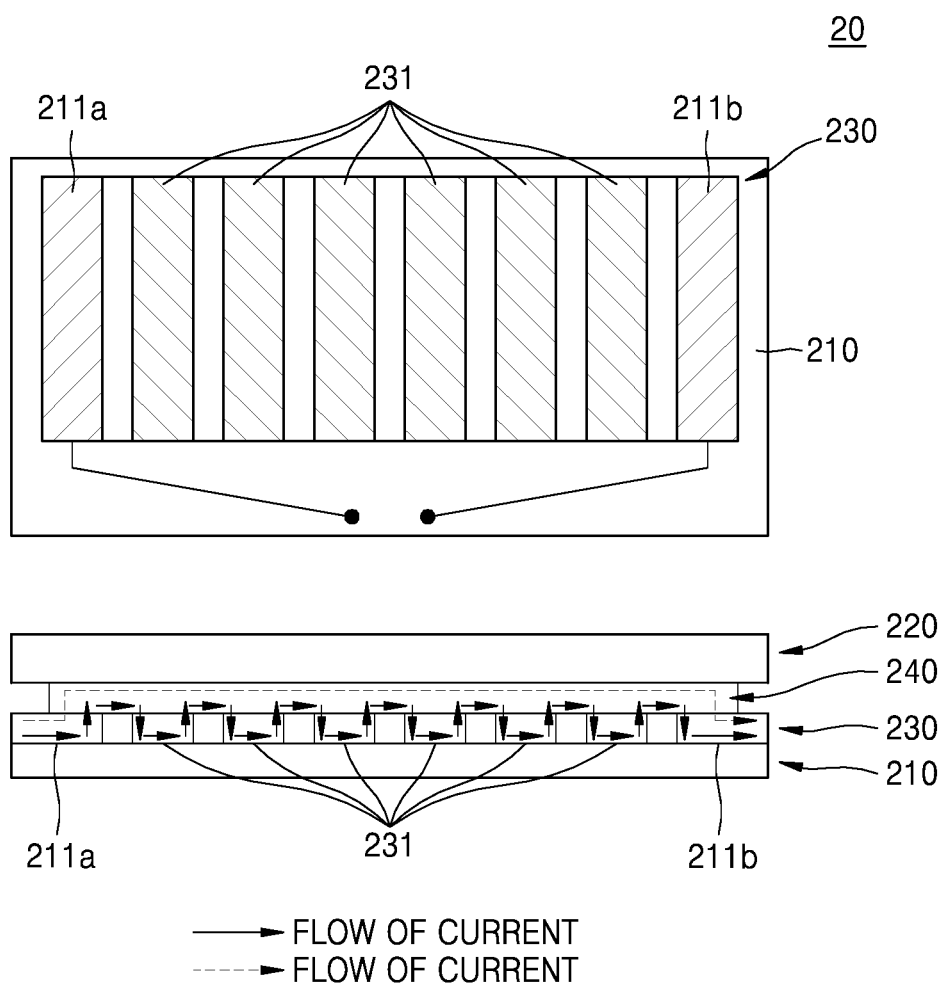
FIG. 4 is a diagram schematically showing the flow of current in a device at the time of applying pressure to the pressure sensor of FIG. 2.

FIG. 3 is a diagram schematically showing the flow of current in a device before applying pressure to the pressure sensor of FIG. 2, and FIG. 4 is a diagram schematically showing the flow of current in a device at the time of applying pressure to the pressure sensor of FIG. 2. Referring to FIGS. 3 and 4, the pressure sensor 20 according to an embodiment may use, as described above, the principle that the contact resistance ($R_{1\text{-}2}$) between the first layer 230 of the first substrate and the second layer 240 of the second substrate 220 changes according to pressure applied to the pressure sensor 20. As a result of such a change in $R_{1\text{-}2}$ or in the resistance relationship by the application of external pressure, the flow of current in the device is also changed, resulting in a change in the overall resistance of the device.

That is, the pressure sensor according to an embodiment may enable to implement high performance by using a change in the contact resistance upon the application of pressure, although the pressure sensor is made of a general conductive material rather than a special piezo-resistive material having pressure-dependent resistance.

In detail, referring to FIG. 3, before the application of pressure to the pressure sensor 20, the contact resistance $R_{1\text{-}2}$ between the first layer 230 including the conductive region with a discontinuous pattern and the second layer 240 is significantly high and has a relationship is $R_2 < R_{1\text{-}2}$. Thus, most of the current flows only through the second layer 240 via the two or more terminals 211a and 211b.

However, referring to FIG. 4 showing an embodiment where pressure is applied to the pressure sensor 20, the contact resistance $R_{1\text{-}2}$ between the first layer 230 and the second layer 240 becomes lower, and accordingly, the current may also flow the conductive region 231 of in the first layer 230. Here, referring to FIG. 4, the current flow is changed so that not only the current may flow through the conductive region 231 in the first layer 230 (solid arrows), but also some of the current may still flow through the second layer 240 (dotted arrows). The degree to which the current flows from the second layer to the first layer may be determined according to the absolute magnitude of $R_1$, $R_2$, and $R_{1-2}$. Due to the discontinuous pattern of the conductive region 231, the current may flow again through the second layer 240, and by repeating such a current flow structure, a change in the contact resistance upon the application of pressure may be maximized.

Figure 14:
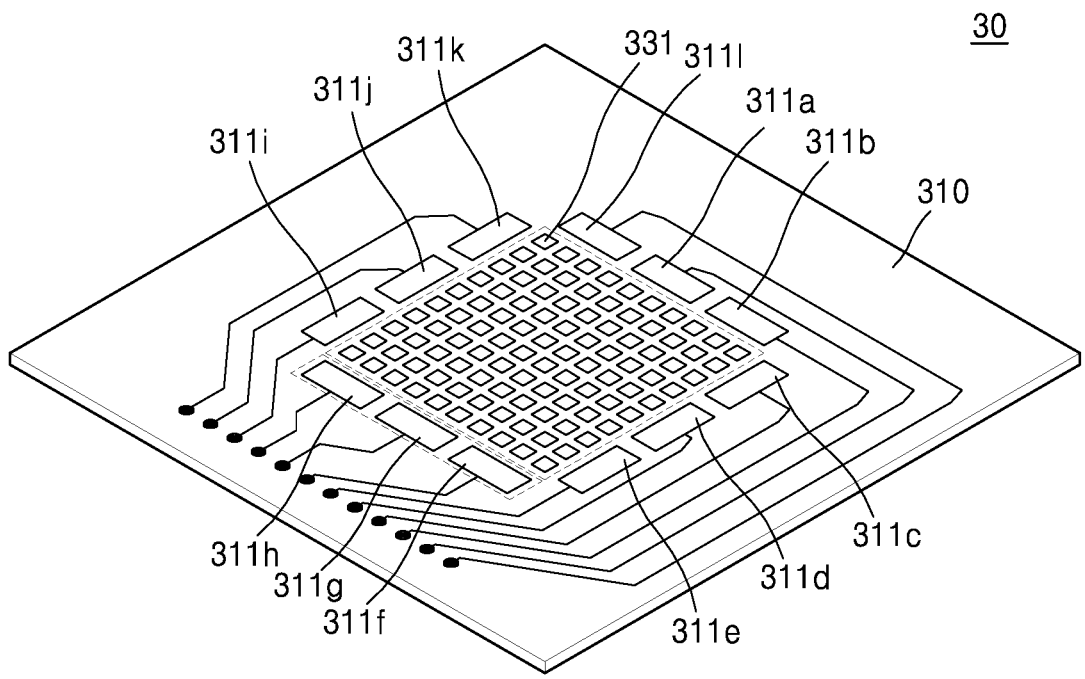
FIG. 14 is a diagram schematically showing a conductive region with an island-type pattern according to an embodiment.

FIG. 14 is a diagram schematically showing a conductive region with an island-type pattern according to an embodiment.

Referring to FIGS. 2 and 14, the conductive region may have a discontinuous pattern. For example, the conductive region 231 may have a line pattern arranged discontinuously in one direction as shown in FIG. 2, or the conductive region 331 may have an island-type pattern arranged discontinuously in a plurality of directions as shown in FIG. 14. However, embodiments are not limited thereto.

That is, a pattern of the conductive region 231 or 331 according to an embodiment is not particularly limited, so long as the pattern is arranged discontinuous.

The discontinuous pattern may have a rectangular, triangular, polygonal, circular, elliptical, stripe, or irregular shape, or a combination thereof. In detail, the discontinuous pattern may have a rectangular, triangular, polygonal, circular, elliptical, tripe, or irregular shape. For example, two or more patterns may be the same or different from each other. That is, a plurality of patterns each independently having a rectangular, triangular, polygonal, circular, elliptical, tripe, or irregular shape are combined to form a discontinuous pattern.

In one embodiment, the discontinuous pattern may have the same or different electrical conductivity. For example, when the discontinuous pattern has different electrical conductivity from each other, i.e., when the electrical conductivity in the conductive region is varied, the resistance change in the pressure sensor may be also varied. For example, at a portion having large electrical conductivity, the difference in the electrical conductivity with the second layer is large, and thus, the resistance change at the time of applying pressure to the portion may be also large. Meanwhile, at a portion having small electrical conductivity, the difference in the electrical conductivity with the second layer is small, and thus, the resistance change at the time of applying pressure to the portion may be also small. By using such differences in the electrical conductivity, as described below, a mapping method using the pressure sensor may exhibit good effect. Here, all of the discontinuous patterns have electrical conductivity that is the same as or greater than that of the second layer.

In one or more embodiments, the sum of the conductive region areas may be in a range of about 25% to about 95% of the total area of the first substrate. For example, the sum of the conductive region areas may be in a range of about 35% to about 80% of the total area of the first substrate. However, embodiments are not limited thereto.

In one or more embodiments, a pattern width of the conductive region with the discontinuous pattern may be in a range of about 1 μm to about 2 cm. For example, a pattern width of the conductive region with the discontinuous pattern may be in a range of about 10 μm to about 1.5 cm, but embodiments are not limited thereto. For example, a pattern width of the conductive region with the discontinuous pattern may be in a range of about 20 μm to about 1 cm, but embodiments are not limited thereto.

In one or more embodiments, a thickness of the second layer may be in a range of about 0.1 μm to about 1 mm. For example, a thickness of the second layer may be in a range of about 0.5 μm to about 0.5 mm, but embodiments are not limited thereto. For example, a thickness of the second layer may be in a range of about 0.8 μm to about 0.3 mm, but embodiments are not limited thereto.

As described above, the sensitivity and driving range of the pressure sensor according to an embodiment may be controlled by appropriately adjusting the area ratio of the conductive region included in the first layer to the entire surface area of the first substrate, the pattern width or interval of the conductive region with the discontinuous pattern, and the thickness of the second layer. When the pressure sensor has high sensitivity, due to the high pressure applied to the pressure sensor, the reactivity of the pressure sensor may be saturated, resulting in a narrow driving range of the pressure. However, when the pressure sensor has a wide driving range, the variation of the reactivity of the pressure sensor upon the pressure applied thereto may be reduced, and accordingly, the change in the pressure may be measured at high temperatures without being saturated.

For example, when the pattern width or interval of the conductive region with the discontinuous pattern or the area ratio of the conductive region is significantly small out of the ranges described above, the overall resistance of the device may not be sufficiently reduced, causing a problem of low response of the pressure sensor. Meanwhile, when the pattern width or interval of the conductive region with the discontinuous pattern or the area ratio of the conductive region is significantly large, there may be a large resistance variation even at a small pressure change, so that the pressure sensor may have good sensitivity. However, due to significantly reduced number of the contact resistance, the influence of the contact resistance variation to the entire device may be reduced. For example, when the thickness of the second layer is significantly large out of the range described above, the pressure sensor may not have sensitivity at a desired level. However, when the thickness of the second layer is significantly small, the pressure may not be applied to the pressure sensor at a great intensity.

The first layer and the second layer may each independently include at least one material selected from gold (Au), silver (Ag), silver epoxy, palladium (Pd), copper (Cu), aluminum (Al), titanium (Ti), chromium (Cr), platinum (Pt), zinc (Zn), silver/silver chloride, silver/silver ion, mercury (Hg)/mercury oxide, nickel (Ni), an alloy or composite thereof, a conductive polymer, a conductive fiber, and a graphitic material.

In one or more embodiments, as a material for forming the first layer is not particularly limited, so long as the material has electrical conductivity that is the same as or greater than that of a material for forming the second layer. For example, the first layer may include at least one material selected from Au, Ag, Ag epoxy, Pd, Cu, Al, Ti, Cr, Pt, Zn, Ag/AgCl, Ag/Ag ion, Hg/Hg oxide, Ni, an alloy or composite thereof, a conductive polymer, a conductive fiber, and a graphitic material. For example, the first layer may include at least one metal selected from Au, Ag, Cu, Al, Zn, Ni, and a graphitic material, but embodiments are not limited thereto. For example, the first layer may include Au, but embodiments are not limited thereto.

In the same manner as in the first layer, a material for forming the second layer is not particularly limited, so long as the material has electrical conductivity that is the same as or smaller than that of a material for forming the first layer. For example, the second layer may include at least one material selected from Au, Ag, Ag epoxy, Pd, Cu, Al, Ti, Cr, Pt, Zn, Ag/AgCl, Ag/Ag ion, Hg/Hg oxide, Ni, an alloy or composite thereof, a conductive polymer, a conductive fiber, and a graphitic material. For example, the second layer may include a conductive polymer, but embodiments are not limited thereto. For example, the conductive polymer may be poly(3,4-ethylenedioxythiophene) polystyrene sulfonate (PEDOT:PSS). For example, the second layer may include a conductive fiber, but embodiments are not limited thereto. For example, the second layer may include a graphitic material, but embodiments are not limited thereto. For example, the graphitic material may have increased or reduced conductivity by controlling a concentration of the graphitic material. That is, the materials for forming the first layer and the second layer are not particularly limited, and any material may be used, so long as a material for forming the first layer has electrical conductivity that is the same as or greater than that of a material for forming the second layer. For example, when the first layer includes Ag, the second layer may include Au having lower electrical conductivity than Ag. When the first layer includes Au, the second layer may include Al having lower electrical conductivity than Au. In addition, even if the first layer and the second layer both include a graphitic material, by controlling a concentration of the graphitic material, electrical conductivity of the graphitic material included in the first layer may become greater than or the same as that of the graphitic material included in the second layer, to thereby implement the present inventive concept. For example, when the concentration of the graphitic material is high, the electrical conductivity thereof is also high, and when the concentration of the graphitic material is low, the electrical conductivity thereof is also low. Thus, the concentration of the graphitic material included in the first layer may be the same as or higher than that of the graphitic material included in the second layer.

Here, the term "graphitic material" as used herein refers to a material having a surface on which carbon atoms are arranged in a hexagonal shape, and that is, refers to a material having a graphitic surface. Any material may be a graphitic material regardless of physical or chemical properties or structural characteristics, so long as the material has a graphitic surface. The graphitic material may include, for example, at least one material selected from a graphene sheet, a highly oriented pyrolytic graphite (HOPG) sheet, a graphene oxide sheet, a reduced graphene oxide sheet, a single-walled carbon nanotube and a double-walled carbon nanotube, a multi-walled carbon nanotube, fullerene, and a composite thereof. The graphitic material may be a metallic material, a semiconductive material, or a hybrid material, and for example, may be a hybrid material of a graphene sheet and a single-walled carbon nanotube.

The term "sheet" as used herein refers to a material having a certain width and thickness, and may be understood as including, for example, a film, a web, a membrane, or a composite constituent thereof.

Hereinafter, the graphitic material will be described in detail, but the material for forming the second layer is not limited to the graphitic material.

In an embodiment, the graphitic material may be a graphene sheet. Here, due to a two-dimensional shape of the graphene sheet, a contact area between constituent materials is larger than that of an one-dimensional material, so that the second layer having a large area may be implemented.

In one or more embodiments, the graphitic material may be a hybrid material of a graphene sheet and a single-walled carbon nanotube. Here, based on the advantage of a two-dimensional shape of the graphene sheet, use of the hybrid material may solve disadvantages that a high concentration of the graphene sheet is necessary to form the second layer when using graphene sheet only.

In one or more embodiments, the graphitic material may be a hybrid material of a graphene sheet and a single-walled carbon nanotube. Here, the size and thickness of the second layer may be increased, resulting in an effect of increasing an effective area of a nanoelectrode per unit area.

In one or more embodiments, the second layer may further include a phage binding to the graphitic material, wherein the phage binding may be between the graphitic material and a peptide displayed on a coat protein of the phage or a fragment thereof.

In one or more embodiments, the second layer may include a peptide binding to the graphitic material.

The peptide binding to the graphitic material may be a material binding to the graphitic material in a non-destructive manner. The peptide may be selected from peptide libraries, and for example, by a phage display technique. Through the phage display technique, the peptide may be genetically linked to, inserted into, or substituted for the coat protein of the phage, resulting in display of the protein on the exterior of the phage, and accordingly, the peptide may be encoded by the genetic information in the virion. A numbers of variants of the protein may be selected and screened by the displayed proteins and DNA encoding the same, and such this method is called "biopanning". Briefly, biopanning involves a reaction between phage-displayed variants with a target (e.g., graphitic material) that has been immobilized, a washing process performed on unbound phage, and an elution process performed on specifically bound phage by disrupting the binding interactions between the phage and the target. A portion of the eluted phage may be set aside for DNA sequencing and peptide identification, and the remainder may amplified in vivo to prepare a sub-library for the next round. Then, this procedure is repeated.

The term "phage" or "bacteriophage" is used interchangeably, and may refer to a virus that infects bacteria and replicates within the bacteria. The phage or bacteriophage may be used to display a peptide which selectively or specifically binds to a graphitic material or volatile organic compound. The phage may be genetically engineered to display the peptide capable of binding to the graphitic material on a coat protein of the phage or a fragment thereof. The term "genetic engineering" or "genetically engineered" as used herein may refer to introduction of one or more genetic modifications into the phage in order to display the peptide capable of binding to the graphitic material on the coat protein of the phage or the fragment thereof, or a phage prepared thereby. The genetic modifications include introduction of a foreign gene encoding the peptide. In addition, the phage may be a filamentous phage, for example, M13 phage, F1 phage, Fd phage, If1 phage, Ike phage, Zj/Z phage, Ff phage, Xf phage, Pf1 phage, or Pf3 phage.

In addition, the term "phage display" or "phage including a phage displayed thereon" as used herein may refer to a display of a functional foreign peptide or protein on a surface of a phage or phagemid particle. Here, the surface of the phage may refer to a coat protein of the phage or a fragment thereof.

The functional foreign peptide may be present at an N-terminus of a coat protein of the phage through binding thereto or through insertion into a coat protein. In addition, the phage may be a phage in which the C-terminus of the functional foreign peptide is linked to the N-terminus of the coat protein of the phage, a phage in which the peptide is inserted between consecutive amino acid sequences of the coat protein of the phage, or a phage in which the peptide is replaced for a part of the amino acid sequences of the coat protein of the phage. The positions in the amino acid sequence of the coat protein, at which the peptide is inserted or replaced, may be positions of 1 to 50, positions of 1 to 40, positions of 1 to 30, positions of 1 to 20, positions of 1 to 10, positions of 2 to 8, positions of 2 to 4, positions of 2 to 3, positions of 3 to 4, or a position of 2 from the N-terminus of the coat protein. In addition, the coat protein may be p3, p6, p8, or p9.

The peptide capable of specifically binding to the graphitic material may be a peptide or a peptide set including at least one selected from amino acid sequences of X2SX1AAX2X3P (SEQ ID NO: 1), X2X2PX3X2AX3P (SEQ ID NO: 2), SX1AAX2X3P (SEQ ID NO: 3), and X2PX3X2AX3P (SEQ ID NO: 4). In addition, the peptide or peptide set may be a peptide or peptide set including at least one selected from amino acid sequences of SEQ ID NOs: 5to 6. Consecutive amino acid sequences of the coat protein of the phage may be linked to the N-terminus or C-terminus of the amino acid sequence of the peptide or peptide set. Therefore, for example, the peptide or peptide set may have an amino acid sequence having a length of 5 to 60, 7 to 55, 7 to 40, 7 to 30, 7 to 20, or 7 to 10 amino acids.

The peptide may have a conservative substitution of a known peptide. The term "conservative substitution" as used herein may refer to replacement of a first amino acid residue by a second different amino acid residue without changing biophysical properties of a protein or a peptide. Here, the first and second amino acid residues may refer to those having side chains having similar biophysical properties. The similar biophysical properties may include an ability to donate or accept hydrophobicity, charge, polarity, or hydrogen bonding. Examples of the conservative substitution may be within the groups of basic amino acids (arginine, lysine, and histidine), acidic amino acids (glutamic acid and aspartic acid), polar amino acids (glutamine and asparagine), hydrophobic amino acids (leucine, isoleucine, valine, and methionine), hydrophilic amino acids (aspartic acid, glutamic acid, asparagine, and glutamine), aromatic amino acids (phenylalanine, tryptophan, tyrosine, and histidine), and small amino acids (glycine, alanine, serine, and threonine). Amino acid substitutions that do not generally alter specific activity are known in the art. For example, in the peptide, X1 may be W, Y, F, or H, X2 may be D, E, N, or Q, and X3 may be I, L, or V.

Therefore, the C-terminus of any one peptide selected from SEQ ID NOs: 1to 6 may be linked to the body of an M13 phage, that is, not to the tip of the phage, but to the N-terminus of a coat protein p8 of the M13 phage having a length of 50 amino acids, which is present on the body in a longitudinal direction. In addition, for example, any one peptide selected from SEQ ID NOs: 1to 6 may be replaced for the positions of 2 to 4 (i.e., EGD), the positions of 2 to 3, the positions of 3 to 4, or the position of 2 in the amino acid sequence of the coat protein p8 of the M13 phage.

In an embodiment, a phage on which the peptide capable of binding to the graphitic material is displayed may specifically bind to the graphitic material, to thereby grant additional functions thereto in a non-destructive manner that does not damage the properties of the graphitic material. When peptide is displayed on a coat protein of a filamentous phage or a fragment thereof, a contact area with the graphitic material may be widened to thereby provide a stronger bonding force.

The second layer may have a network structure inside thereof. The term "network" as used herein may refer to a structure composed of random conductive or non-conductive connections (hereinafter referred as "a percolated network").

In an embodiment, such a percolated network structure may further include nanoparticles. For example, the nanoparticle may be a conductive particle or a non-conductive particle. For example, the nanoparticle may include at least one selected from Au, Ag, Cu, Al, Zn, and Ni, but embodiments are not limited thereto.

In an embodiment, the second layer may include a material coated with a conductive ink.

At least one of the first substrate and the second substrate may each independently have a concave-convex structure including a convex portion, a concave portion, or a combination thereof. For example, a cross section of the convex portion or concave portion may be in a triangular, rectangular, polygonal, circular, elliptical, or irregular shape. In an embodiment, the external pressure applied to the first substrate or the second layer may change the contact area or contact distance between the first layer and the second layer.

The first substrate, the second substrate, or both the first and second substrates may be a flexible substrate, and for example, may be a transparent flexible substrate. The substrate may be, for example, a substrate made of polydimethylsiloxane (PDMS), polyethersulfone (PES), poly(3,4-ethylenedioxythiophene), poly(styrenesulfonate), polyimide, polyurethane, polyester, perfluoropolyether (PFPE), polycarbonate, or a combination of the polymers above.

In addition, the pressure sensor may further include a cover on the surface on which the first layer of the first substrate or on a surface opposite to the surface on which the second layer is formed. The cover may be the same material as the first substrate or the second layer, for protecting or accommodating the pressure sensor.

In an embodiment, the pressure sensor may include a processing unit for measuring a signal sensitive to the pressure applied thereto (for example, an electrical signal), or obtaining information about a pressure applied to the pressure sensor. From the processing unit, information about force or pressure (for example, intensity of force, direction of force, or number of applying force) by measuring variable resistance, voltage, or current. The information may be converted into a predetermined signal (for example, an electrical signal) to be displayed, or may be conveyed to a different device connected to the pressure sensor to allow the different device to perform a desired operation. Therefore, the processing unit may include an electronic device for converting the measured values to displayed values, a display for indicating results, or at least one adjustment interface. In addition, the pressure sensor according to an embodiment may perform the same function as the processing unit in an external measuring device connected through a terminal.

In an embodiment, the pressure sensor may be a pressure sensor for measuring blood pressure or heartbeat.

The blood pressure may be distinguished by arterial blood pressure, capillary blood pressure, and venous blood pressure, and generally refers to venous blood pressure. Venous blood pressure may vary by heartbeat. Methods of measuring the blood pressure include an invasive method and a non-invasive method. The pressure sensor according to an embodiment may pressure sensor may be connected to a catheter to measure the blood pressure. For example, according to the invasive method, the blood pressure may be measured through a connection tube containing heparin saline by inserting a catheter into a blood vessel, and the pressure sensor according to an embodiment may be connected to a distal portion of the catheter to measure the blood pressure. According to the non-invasive method, the pressure sensor according to an embodiment may be disposed on the skin at a region where pulse waves may be measured. For example, the pressure sensor according to an embodiment may be disposed on the skin at a region through which radial artery, brachial artery, carotid artery, carotid vein, femoral artery, popliteal artery, tibial artery, or dorsal pedis artery passes to measure pulse waves. The pressure sensor according to an embodiment may measure the blood pressure by sensing the pressure (blood pressure) delivered to the skin above the blood vessel by the contraction and expansion of the blood vessel during the heartbeat.

In addition, the pressure sensor according to an embodiment may measure heartbeats or heart rates by sensing a pulse generated in the blood vessel or vein to which the heartbeats are delivered and converting the pulse to an electrical signal.

According to an aspect of the present disclosure, there is provided a method of manufacturing the pressure sensor.

In an embodiment, the method of manufacturing the pressure sensor may include: disposing a first layer on a first substrate, wherein the first layer includes a conductive region; disposing a second layer on the first layer, wherein the second layer has the same or lower electrical conductivity than that of the conductive region.

In an embodiment, the method of manufacturing the pressure sensor may include: (a) a process of manufacturing a second layer by manufacturing a material having electrical conductivity in the form of a film; (b) a process of manufacturing a first layer including a conductive region including a material having the same or higher electrical conductivity than that of the material included in the second layer; (c) a process of disposing the first layer on a first substrate such that the conductive region is disposed toward a surface opposite to the first substrate; (d) a process of disposing the second layer on the first layer such that the second layer faces the conductive region of the first layer; and (e) 2 a process of disposing two or more terminals on one of the first and second layers such that the two or more terminals are spaced apart from the conductive region and electrically connected to the second layer.

The expression "electrically connected to" as used herein refers to not only a direct connection between two constitutional elements of the present inventive concept, but also a connection to any other connecting members such as a bus bar.

Here, the order of the processes (a) to (e) is not particularly defined. For example, the process (e) may be performed before the process (c) or (d), the process (a) may be performed after the process (b), or the process (c) may be performed after the process (d).

In an embodiment, the method of manufacturing the pressure sensor may further include, before or after any one of the processes (a), (b), and (c), a process (f) of disposing the second layer on a second substrate.

According to an aspect of the present disclosure, there is provided a device including the pressure sensor.

In detail, the device may be a wearable device.

The wearable device may be designed to measure biometrics including blood pressure or heartbeat. In an embodiment, the biometrics may also include force or pressure generated by the walking of a person. In an embodiment, one or more pressure sensors may be mounted on the sole of a person's foot or the sole of a shoe to measure a force intensity or dispersion extent by the walking of a person. In one or more embodiments, one or more pressure sensors may be attached to the teeth or the inside of a mouse to measure a force intensity or dispersion extent by occlusion or the contact between teeth. Therefore, the wearable device according to an embodiment may include a patch, a band, a watch, a shoe, or a teeth attachment device.

The wearable device according to an embodiment may further include a controller for receiving and processing signal data generated from the pressure sensor so that the wearable device be logically communicate with the pressure sensor and output data relating to the control of the pressure sensor The pressure sensor in the wearable device may be controlled by the controller, and the controller may be sensitive to a particular event (for example, switch operation) at a regular time interval to receive and process biometrics detected by the pressure sensor.

In addition, the wearable device may further include a memory capable of storing a processor for operation of the controller, and temporarily storing input/output data (for example, biometrics). The memory may save information on the electrical signal (for example, blood pressure or heartbeat) received from the pressure sensor.

In addition, the wearable device may include a display unit for displaying information that is processed in the controller or stored in the memory. In addition, the wearable device may further include a wireless communication unit for delivering the information to a user wearing a wearable device equipped with a wireless communication system or other users (for example, a person near the user wearing the wearable device, an athlete trainer, a doctor, a hospital staff, or a family member of the user wearing the wearable device). For example, the wireless communication unit may include a broadcast receiver module, a mobile communication module, a wireless internet module, a near field communication module, and the like. The information sensed by the pressure sensor may be delivered to the user wearing the wearable device or other uses through such a wireless communication unit.

The pressure sensor in the wearable device according to an embodiment is controllable and has excellent electrical characteristics, mechanical flexibility, and stability, and thus, may be applied to a wearable device for measuring biometrics (for example, blood pressure or heart rate).

According to an aspect of the present disclosure, there is provided a mapping method using the pressure sensor.

In an embodiment, the mapping method includes: measuring resistance of sections connecting any two of two or more terminals before applying pressure to the pressure sensor; measuring resistance of sections connecting any two of two or more terminals after applying pressure to the pressure sensor; and figuring out an intensity of the pressure applied to the pressure sensor by finding a point at which the sections where the resistance changes after the application of the pressure intersect, finding a position to which the pressure is applied, and measuring the degree of the resistance change.

Figure 17:
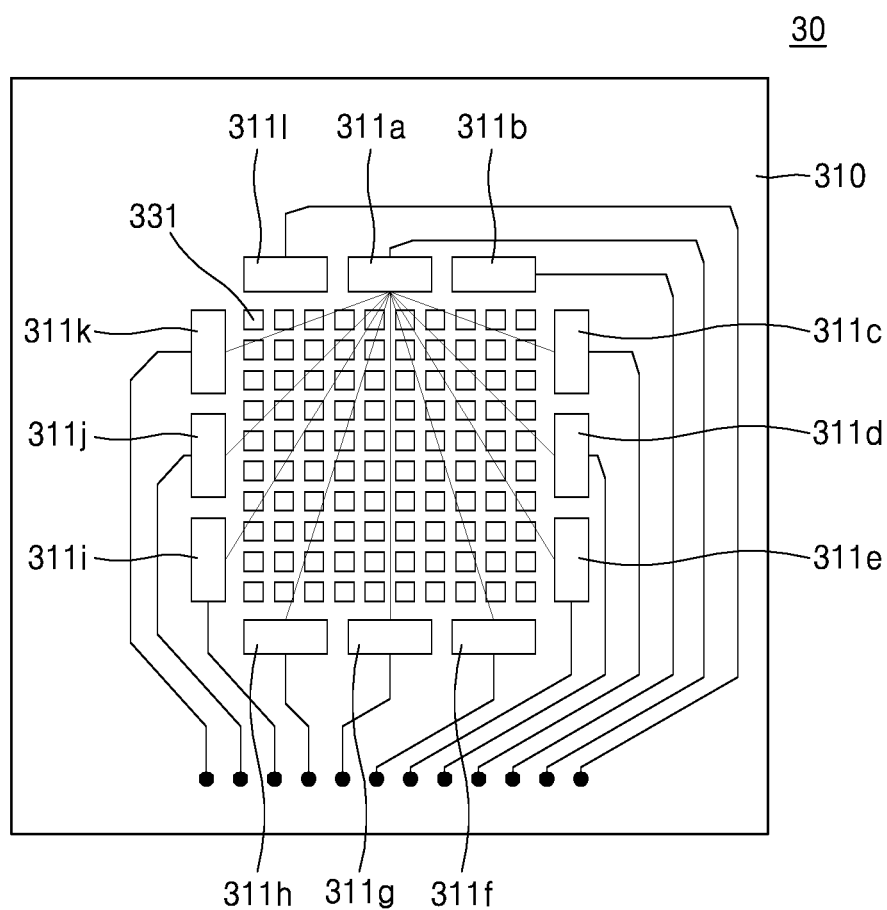
FIG. 17 is a diagram showing a process of measuring resistance between two terminals according to an embodiment.

FIG. 17 is a diagram schematically showing a concept of mapping that may determine the intensity and position of the applied pressure by using the pressure sensor including a conductive region with an island-type pattern according to an embodiment.

Referring to FIGS. 14 and 17 together for the explanation of the mapping method, a pressure sensor 30 including a conductive region with an island-type pattern may include a conductive region 331 with an island-type pattern on a first substrate 310, and a plurality of terminals 311a to 311l. Hereinafter, an embodiment of a pressure sensor including a conductive region with an island-type pattern is described, but the embodiment is provided for illustrational purposes only. Thus, the same mapping method may be associated with a pressure sensor including a conductive region with a line pattern or a pressure sensor without any discontinuous pattern.

If pressure is applied to a specific region in the island-type pattern of the conductive region, due to a change in the contact resistance $R_{1-2}$ as described above, a resistance change between the plurality of terminals occurs. For example, as shown in FIG. 17, the resistance of sections between a terminal 311a and any other terminals, e.g., a section connecting a terminal 311a and a terminal 311c or a section connecting a terminal 311a and a terminal 311d, is measured before the application of the pressure. Then, the resistance of each of the sections between a terminal 311a and any other terminals is measured after the application of the pressure. Here, the section where the resistance has changed is determined. Regarding other terminals 311b-311l, the same process of measuring the resistance and determining the resistance change is performed. When a point at which the sections where the resistance changes intersect among the sections connecting each terminal, e.g., the section connecting the terminal 311b and the terminal 311e, or the section connecting the terminal 311k and the terminal 311l, a position to which the actual pressure is applied may be mapped. The accuracy and resolution of the mapping may be improved as the number of sections where the resistance may be measured increases, wherein the maximum number of the sections where the resistance may be measured is the number of combinations selecting any two of the plurality of terminals of the pressure sensor.

In addition, as described above, by configuring different electrical conductivities in the pattern, the resistance variation may be varied in the pressure sensor, thereby improving the accuracy and resolution of the mapping.

Furthermore, through not only the position to which the pressure is applied, but also the degree of change in resistance, the intensity of the applied pressure may be determined.

Hereinafter, one or more embodiments will be described in more detail with reference to the following examples. However, these examples are for illustrative purposes only and are not intended to limit the scope of the present disclosure.

[Preparation Example 1] Preparation of a Conductive Nanomesh Film

In an embodiment with respect to the second layer of the present inventive concept, a conductive nanomesh film was prepared as follows.

Preparation of Colloid Solution

First, an aqueous solution was prepared by adding, as a surfactant, sodium-chlolate to distilled water at a concentration of 2% w/v. Then, a colloid solution was prepared by diluting a carbon nanotube (manufacturer: Nanointegris, SuperPure SWNTs, solution type, concentration: 250 μg/ml) with a graphitic material for 48 hours to stabilize a single-walled carbon nanotube (CNT) with sodium-chlolate.

Here, assuming that the single-walled CNT had an average length of about 1 μm and an average diameter of about 1.4 nm, the number of the single-walled CNT included in the colloid solution was calculated according to Equation 1 below:

Number of single-walled carbon nanotube (CNT tubes/ml)=concentration (μm/ml)×3×10$^{11}$ CNT. [Equation 1]

According to Equation 1, the number of single-walled CNT included in the colloid solution was about 7.5×10$^{13}$ tubes/ml.

Preparation of a Phage

A phage GP1, which is an M13 phage having strong affinity to a graphitic surface, i.e., an M13 phage (GP1) with SWAADIP (SEQ ID NO: 5) displayed thereon and a phage GP2 with NPIQAVP (SEQ ID NO: 6) displayed thereon were prepared in the following manner, wherein SWAADIP (SEQ ID NO. 5) is a peptide having strong affinity to a graphitic surface.

First, the 1381$^{st}$ base pair C of an M13KE vector (NEB, product#N0316S) was site-directed mutated to G to prepare an M13HK vector.

Here, the M13KE vector (NEB, product#N0316S) was a cloning vector consisting of 7222-bp DNAs and genetic information thereof was available from the Internet site (https://www.neb.com/~/media/NebUs/Page%20Images/Tools%20and%20Resources/Interactive%20Tools/DNA%20Sequences%20and%20Maps/Text%20Documents/m13kegbk.txt). The base sequences of the oligonucleotides used for the site-directed mutation were as follows:

(SEQ ID NO: 11)
5'-AAG GCC GCT TTT GCG GGA TCC TCA CCC TCA GCA GCG

AAA GA-3',
and (SEQ ID NO: 12)
5'-TCT TTC GCT GCT GAG GGT GAG GAT CCC GCA AAA GCG

GCC TT-3'.

Then, a phage display p8 peptide library was prepared from the prepared M13HK vector by using the restriction enzymes BspHI (NEB, product# R0517S) and BamHI (NEB, product#R3136T).

As an example of the present inventive concept, the base sequence of the oligonucleobodies used for the preparation of the phage display p8 peptide library were as follows:

(SEQ ID NO: 13)
5'- TTA ATG GAA ACT TCC TCA TGA AAA AGT CTT TAG

TCC TCA AAG CCT CTG TAG CCG TTG CTA CCC TCG TTC

CGA TGC TGT CTT TCG CTG CTG -3',
and (SEQ ID NO: 14)
5'- AAG GCC GCT TTT GCG GGA TCC NNM NNM NNM NNM

NNM NNM NNM NCA GCA GCG AAA GAC AGC ATC GGA ACG

AGG GTA GCA ACG GCT ACA GAG GCT TT -3'

The base sequence of the prepared phage display p8 peptide library had a variety of 4.8×10$^7$ plaque-forming unit (PFU), and had a copy number of about 1.3×10$^5$ per sequence.

Then, according to a bio-panning method, a phage on which peptides to be used as biomaterials were displayed was selected by binding the phage display p8 peptide library prepared above to a graphitic surface. The biopanning method was conducted as follows.

First, before use in the experiment, a fresh surface was detached from a highly oriented pyrolytic graphite (HOPG; SPI, product#439HP-AB), which is a material having a graphitic surface, by using a tape to thereby minimize the defect of a sample surface, the detect being caused by oxidation or the like. Here, as a HOPG substrate, a substrate having a relatively large grain size of 100 μm or less was used.

Subsequently, phage display p8 peptide library of 4.8×$10^{10}$ PFU (4.8×$10^7$ diversities, 1,000 copies per sequence) prepared above was prepared in 100 μl of Tris-buffered saline (TBS) and conjugated with the HOPG surface for 1 hours in a shaking incubator at a rate of 100 rpm. 1 hour later, the solution was removed and the HOPG surface was washed 10 times in TBS. The washed HOPG surface was reacted with pH 2.2 Tris-HCl as an acidic buffer for 8 minutes to elute peptides that weakly reacted, and the remaining phage was eluted with an XL-1 blue *E. coli* culture in mid-log phase for 30 minutes. A portion of the eluted culture was set aside for DNA sequencing and peptide identification, and the remainder was amplified to prepare a sub-library for the next round. The above procedure was repeated using the prepared sub-library. Meanwhile, the left plaque was subjected to DNA sequencing to obtain the p8 peptide sequence, and the sequence was analyzed to obtain a phage GP1 with SWAADIP (SEQ ID NO: 5) displayed thereon and a phage GP2 with NPIQAVP (SEQ ID NO: 6) displayed thereon, wherein SWAADIP (SEQ ID NO: 5) is a peptide having strong affinity to a graphitic surface.

Preparation of a Conductive Nanomesh Film

The colloid solution prepared above and a phage solution containing the M13 phage (GP1) having strong affinity to the graphitic surface were mixed at various molar ratios. The molar ratio of SWNT:GP1 may be 4:8 or 2:4.

Next, for dialysis, each of the mixtures was added to a semi-permeable dialysis membrane (SpectrumLab, MWCO 12,000~14,000, product #132 700) tube, and each membrane tube was dialyzed against triple distilled water. About 20 hours after dialysis started, a thin nanomesh film was formed along the surface of the membrane tube. Then, each membrane tube was transferred to triple distilled water, and the nanomesh film was detached by twisting the membrane of the membrane tube. The detached nanomesh film was transferred to a desired substrate, and then, dried for use.

[Preparation Example 2] Preparation of a Nanomesh-Gold Particle Film Including Gold Nanoparticles The colloid solution (SWNT: 3×$10^{13}$ PFU) prepared according to Preparation Example 1, a phage solution (6×$10^{13}$ PFU) containing the M13 phage (GP1) having strong affinity to the graphitic surface (6×$10^{13}$ PFU), a solution containing gold particles (3.6×$10^{11}$ PFU) having a diameter of 40 nm (Sigma Aldrich, product #741981) were mixed at a predetermined ratio.

Next, for dialysis, each of the mixtures was added to a semi-permeable dialysis membrane (SpectrumLab, MWCO 12,000~14,000, product #132 700) tube, and each membrane tube was dialyzed against triple distilled water. About 20 hours after dialysis started, a thin nanomesh film was formed along the surface of the membrane tube. Then, each membrane tube was transferred to triple distilled water, and the nanomesh film was detached by twisting the membrane of the membrane tube. The detached nanomesh film was transferred to a desired substrate, and then, dried for use.

[Preparation Example 3] Preparation of a Nanomesh Film Using a Peptide

A peptide (ADSWAADIPDPAGGGADSWAADIPDPA, SEQ ID NO: 11) derived from a phage specifically binding to the graphitic surface was chemically synthesized (TRON Ltd.) at a concentration of 3 mg/mL. 600 μL of the prepared peptide and the SWNT colloid solution (3.0×$10^{13}$ PFU) prepared according to Preparation Example 1 were mixed, and the mixed solution was added to a semi-permeable dialysis membrane (SpectrumLab, MWCO 12,000~14,000, product #132 700) tube for dialysis against triple distilled water.

[Preparation Example 4] Preparation of a Flat Polydimethylsiloxane (PDMS) Film without a Pattern To prepare the second substrate of the present inventive concept, a sylgard (Sylgard® 184) silicone elastomer and a sylgard (Sylgard® 184) silicone elastomer curing agent were mixed at a ratio of 10:1, and then, a thickness of the mixture was adjusted by using a petri dish spin coating technique, and was cured on a hot plate at a temperature of 80□ for about 24 hours. A cured PDMS film obtained therefrom was cut into a desired size for use by using a scalpel.

[Preparation Example 5] Preparation of PDMS Film with a Pyramid Structural Pattern To prepare the second substrate of the present inventive concept and prepare a PDMS film with a pyramid structural pattern, a silicon (Si) mold with a pyramid pattern was first prepared. For the Si mold, a Si substrate ($SiO_2$ (1,000 nm)/Si(500 um)) was subjected to a standard photolithography process to form a pattern where the pyramid is to be formed, and a $SiO_2$ layer was removed using a buffered oxide etchant (BOE) solution. Then, by using a KOH solution, the Si substrate was ditched to obtain the Si mold with the pyramid pattern formed thereon.

Next, a sylgard (Sylgard® 184) silicone elastomer and a sylgard (Sylgard® 184) silicone elastomer curing agent were mixed at a ratio of 10:1, and then, the Si mold was spin-coated by using a petri dish spin coating technique. The spin-coated substrate was then cured on a hot plate at a temperature of 80□ for about 24 hours. A cured PDMS film obtained therefrom was cut into a desired size for use by using a scalpel.

[Preparation Example 6] Preparation of a Filter Paper-Based Conductive Film

A commercially available filter paper (90 mm, Hyundai Micro. Co. Ltd, Germany) was dipped in a carbon ink (Electrodag PF-407C, Acheson) solution, and dried to prepare a conductive film. Such a dried conductive paper was then cut into a desired size for use by using a scalpel.

Example 1

As the conductive region included in the first layer, a gold (Au) pattern having a width of 1 mm was used. Here, the conductive region was disposed on a PCB substrate, which was a first substrate, so that the conductive region was spaced apart from the terminals, had a discontinuous line pattern, and had a pattern interval of about 1 mm.

As the second layer, the nanomesh film of Preparation Example 1 was used. As the second substrate, the flat PDMS film of Preparation Example 3 was used, and was disposed on the second layer of the second substrate.

To face the first layer and the second layer each other, the first substrate including the first layer disposed thereon was attached to the second substrate including the second layer disposed thereon.

Example 2

A pressure sensor was prepared in the same manner as in Example 1, except that an Au pattern having a width of 0.1 mm was used as the conductive region included in the first layer and the pattern interval of the conductive region was changed to 0.1 mm.

Example 3

A pressure sensor was prepared in the same manner as in Example 1, except that an Au pattern having a width of 12 mm was used as the conductive region included in the first layer.

Example 4

A pressure sensor was prepared in the same manner as in Example 1, except that an Au pattern having a width of 0.75 mm was used as the conductive region included in the first layer and the conductive region had a discontinuous island-type pattern of which a pattern interval was 0.25 mm.

Example 5

A pressure sensor was prepared in the same manner as in Example 1, except that the PDMS film with the pyramid pattern of Preparation Example 5 was used as the second substrate.

Example 6

A pressure sensor was prepared in the same manner as in Example 1, except that the nanomesh-gold particle film including gold nanoparticles of Preparation Example 2 was used as the second layer.

Example 7

A pressure sensor was prepared in the same manner as in Example 1, except that the nanomesh film using the peptide of Preparation Example 3 was used as the second layer.

Example 8

A pressure sensor was prepared in the same manner as in Example 1, except that the second substrate was not used, and instead of the second layer, the filter paper-based conductive film of Preparation Example 6 was used.

Comparative Example 1

A pressure sensor was prepared in the same manner as in Example 1, except that, as the first layer, an Au electrode that was not spaced apart from the terminals and had a continuous pattern rather than a discontinuous pattern was used.

Comparative Example 2

As the conductive region included in the first layer, an Au pattern having a width of 1 mm was used. Here, the conductive region was disposed on a PCB substrate, which was a first substrate, so that the conductive region had a discontinuous line pattern and had a pattern interval of about 1 mm.

A pressure sensor was prepared by directly transferring the nanomesh film of Preparation Example 1 to the first layer.

[Experimental Example] Evaluation of Characteristics of the Pressure Sensor

Regarding the pressure sensors prepared according to Examples 1 to 8 and Comparative Examples 1 and 2, the resistance values of the pressure sensors were measured while the pressure applied thereto was sequentially increased from 0 kPa to 300 kPa. Here, the patterns on both ends of the lower substrate were used as terminals for measurement. The response of the pressure sensor is denoted by $\Delta R/R_0$, wherein $R_0$ refers to resistance of the pressure sensor before application of the pressure, and $\Delta R$ refers to a resistance change between the resistance of the pressure sensor before application of the pressure and the resistance of the pressure sensor after application of the pressure.

Figure 5:
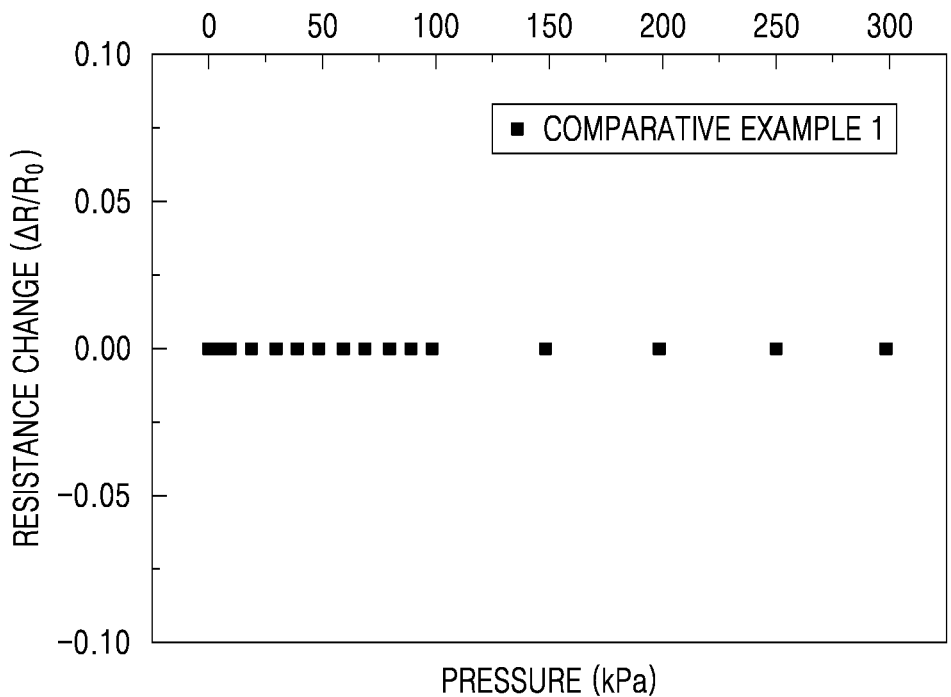
FIG. 5 is a graph showing resistance changes in a device including a pressure sensor prepared according to Comparative Example, measured when pressure is sequentially applied thereto from 0 kPa to 300 kPa.
Figure 6:
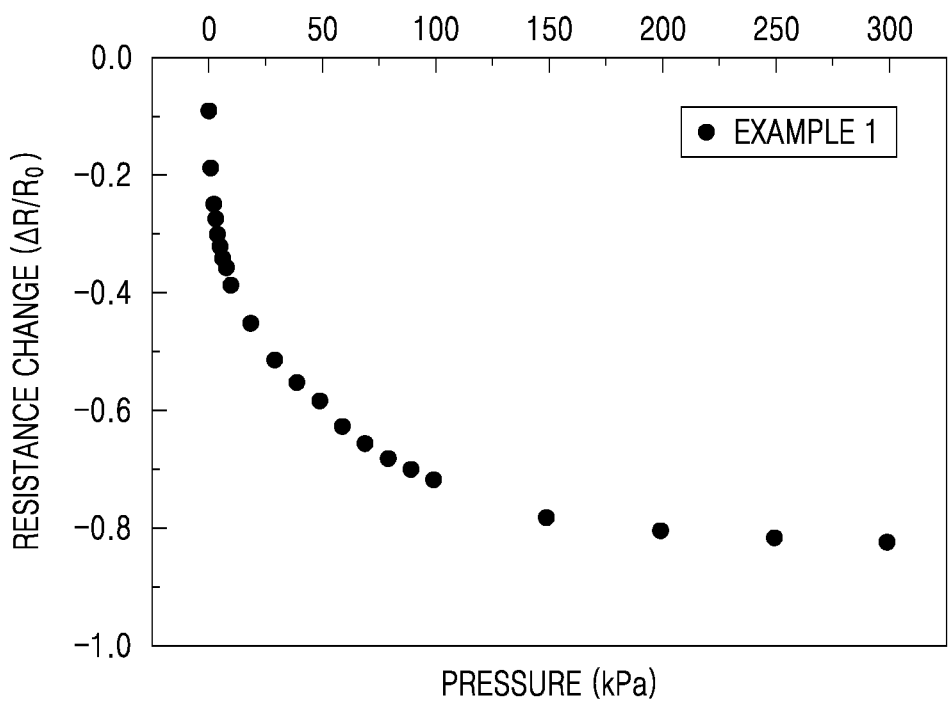
FIG. 6 is a graph showing resistance changes in a device including a pressure sensor prepared according to Example 1, measured when pressure is sequentially applied thereto from 0 kPa to 300 kPa.
Figure 7:
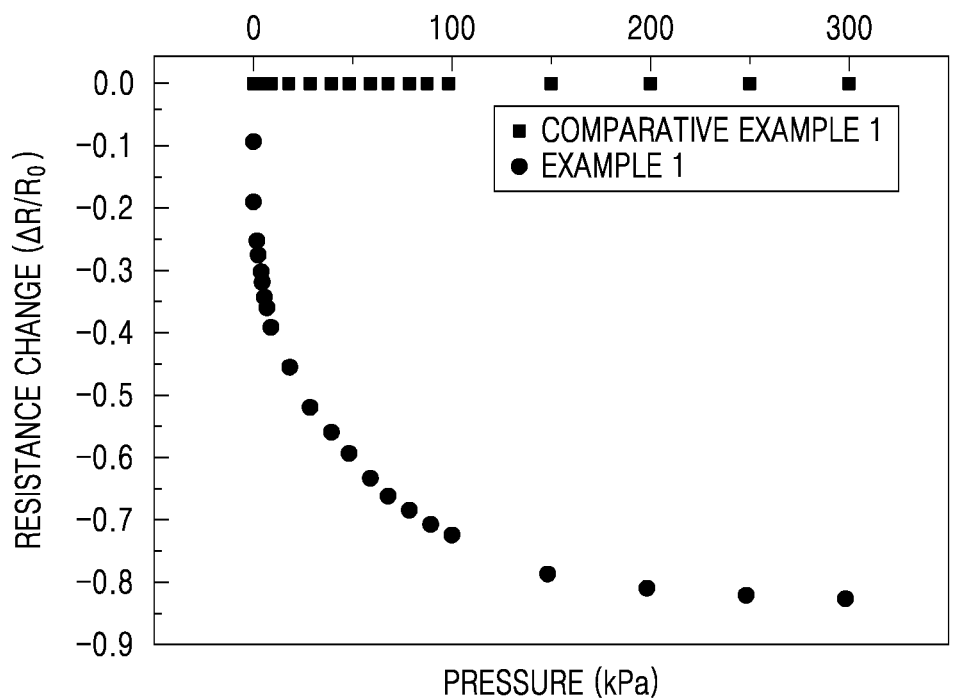
FIG. 7 is a graph showing a comparison of pressure-dependent resistance changes of the pressure sensors of Example 1 and Comparative Example 1.

FIG. 5 shows changes in the pressure sensor of Comparative Example 1 measured when the pressure from 0 kPa to 300 kPa was sequentially applied thereto. FIG. 6 shows changes in the pressure sensor of Example 1 measured when the pressure from 0 kPa to 300 kPa was sequentially applied thereto. FIG. 7 is a graph showing a comparison of the pressure-dependent resistance changes of the pressure sensors of Example 1 and Comparative Example 1.

Referring to FIG. 5, it was confirmed that, when the conductive region was continuously connected with all of the terminals on the first substrate of the pressure sensor as described in Comparative Example 1, almost no change was shown in the pressure-dependent resistance. That is, in the case of the pressure sensor of which the conductive region was continuously connected with the terminals on the first substrate, due to the electric current already flowing through the first layer before application of the pressure, the changes in the pressure-dependent contact resistance did not contribute to the overall resistance of the pressure sensor.

Figure 8A:
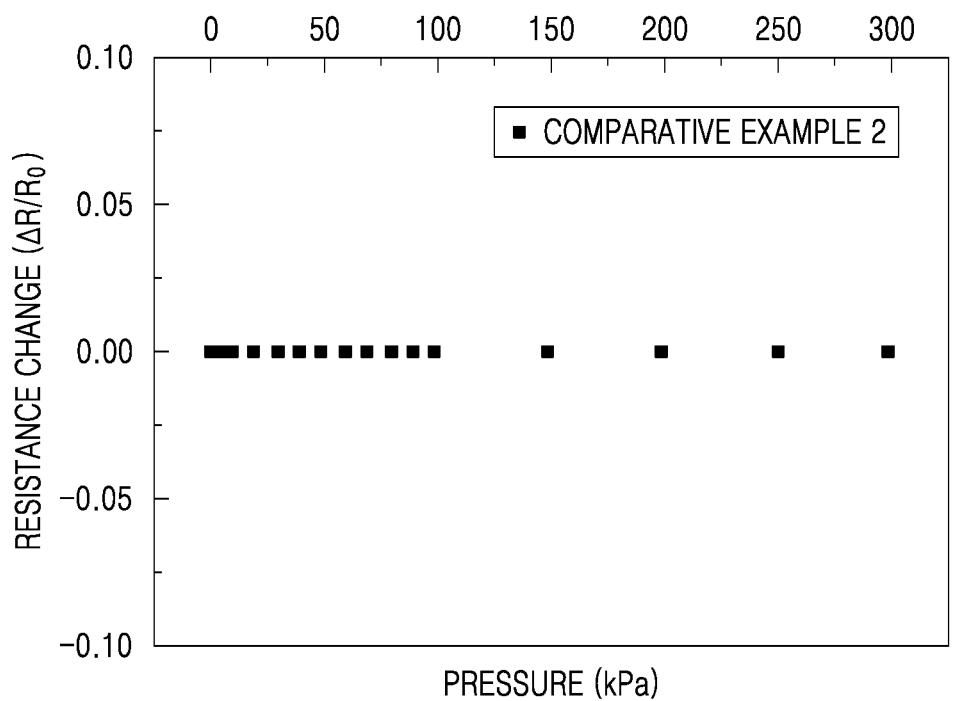
FIG. 8A is a graph showing resistance changes in a device including a pressure sensor prepared according to Comparative Example 2, measured when pressure is sequentially applied thereto from 0 kPa to 300 kPa.

Meanwhile, referring to FIGS. 6 and 7, it was confirmed that the pressure sensor of Example 1 had a significantly large resistance change of about at least 80%. That is, it was confirmed that, even if the same conductive film was used for the second substrate and the second layer, the pressure sensor was able to exhibit significantly excellent performance based on the concept of disposing the conductive region and the terminals in a discontinuous manner To demonstrate the importance of the changes in the contact resistance, the response of the pressure sensor of Comparative Example 2 was also measured. FIG. 8A is a graph showing changes in the resistance of the pressure sensor of Comparative Example 2 measured when the pressure from 0 kPa to 300 kPa was sequentially applied to thereto, and FIG. 8B is an enlarged portion of the graph of FIG. 8B showing the resistance changes on the vertical axis from 0.0000 to −0.0020.

Figure 8B:
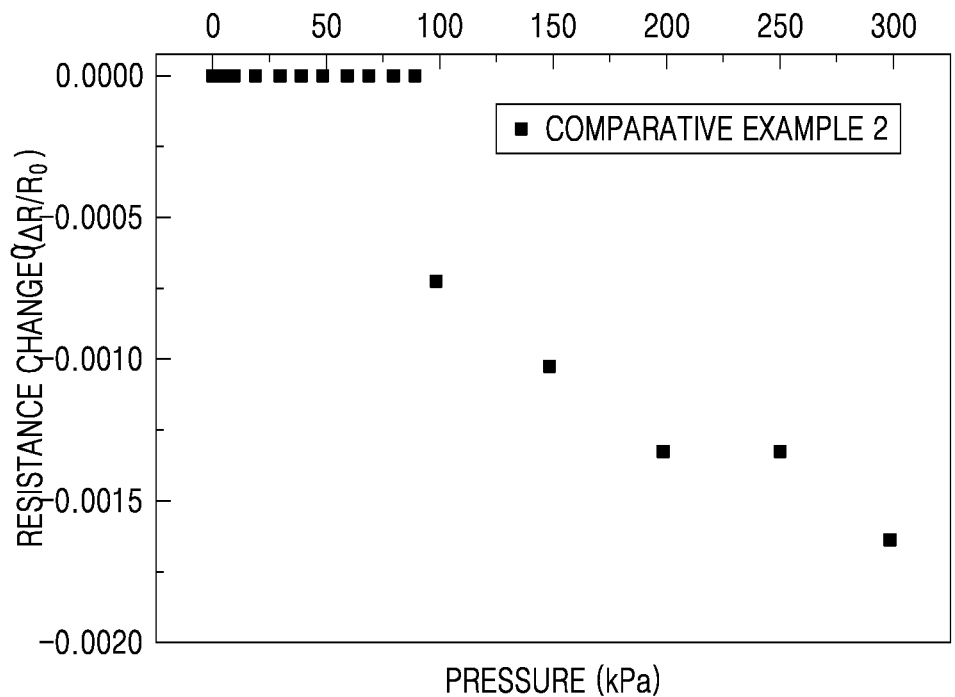
FIG. 8B is an enlarged graph of FIG. 8A showing the resistance changes along the vertical axis in a range of 0.0000 to −0.0020.

Referring to FIGS. 8A to 8B, it was confirmed that, when the nanomesh film was directly transferred to the Au discontinuous pattern, the response of the pressure sensor was very low (0.1% or less), a thousand times lower than the response of the pressure sensor to which the nanomesh film was not directly transferred. That is, since the nanomesh film was directly transferred to the Au pattern, the nanomesh film and the Au pattern already had excellent contact resistance therebetween, resulting in a very low value of $R_{1-2}$, and in this regard, it is interpreted that the current was already more likely to pass through the conductive region so that almost no change in the current flow was shown upon the application of the pressure. That is, due to small change in the contact resistance upon the application of the pressure and almost no change in the current flow throughout the entire pressure sensor, the pressure sensor also showed small resistance change, resulting in significantly low response of the pressure sensor.

In addition, it was understood that the resistance change characteristics obtained upon the application of the pressure to the pressure sensor of Comparative Example 2 may include the piezo-resistive characteristics of the conductive nanomesh film itself. Therefore, based on the results of FIGS. 8A and 8B, it was confirmed that the conductive nanomesh film itself. That is, referring to FIGS. 6, 7, 8A, and 8B, it was confirmed that, even if the second layer had almost no piezo-resistive characteristic, due to a structure in which the first layer was disposed discontinuously on the first substrate, the pressure sensor was able to exhibit excellent response based on the principle that the current flow was changed upon the application of the pressure.

Figure 9:
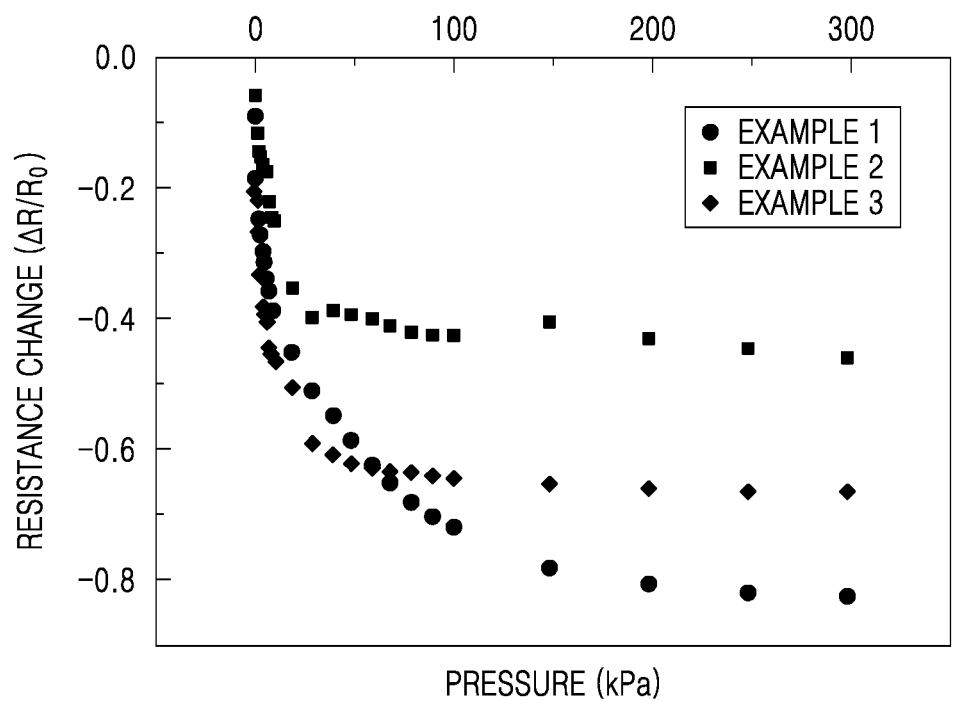
FIG. 9 is a graph showing a comparison of pressure-dependent resistance changes of the pressure sensors of Examples 1 to 3.

Meanwhile, FIG. 9 is a graph showing a comparison of the pressure-dependent resistance changes of the pressure sensors of Examples 1 to 3. Referring to FIG. 9, it was confirmed that the sensitivity and operation range of the pressure sensor was controlled by adjusting the size or pattern interval of the conductive region included in the first layer. When the line pattern had a very small width (0.1 mm=100 μm) as in Example 2, the number of the contact resistance increased as compared with Example 1, and considering the limited reduction of the overall resistance of the pressure sensor, the response of the pressure sensor of Example 2 may be lower than that of the pressure sensor of Example 1.

In addition, when the Au pattern had a very large width as in Example 3, a large resistance change was possibly made with a small pressure change, resulting in good sensitivity of the pressure sensor. However, since the number of the contact resistance of the pressure sensor of Example 3 was significantly smaller than that of the pressure sensor of Example 1, the effects of the changes in the contact resistance on the resistance change of the entire pressure of Example 3 sensor may be small as compared with the pressure sensor of Example 1. However, as the width of the Au pattern increased, the initial sensitivity also increased. In this regard, depending on a desired operation range of response of the pressure sensor, the size of the conductivity region included in the first layer or the intervals between the conductive region included in the first layer may be designed.

Figure 10:
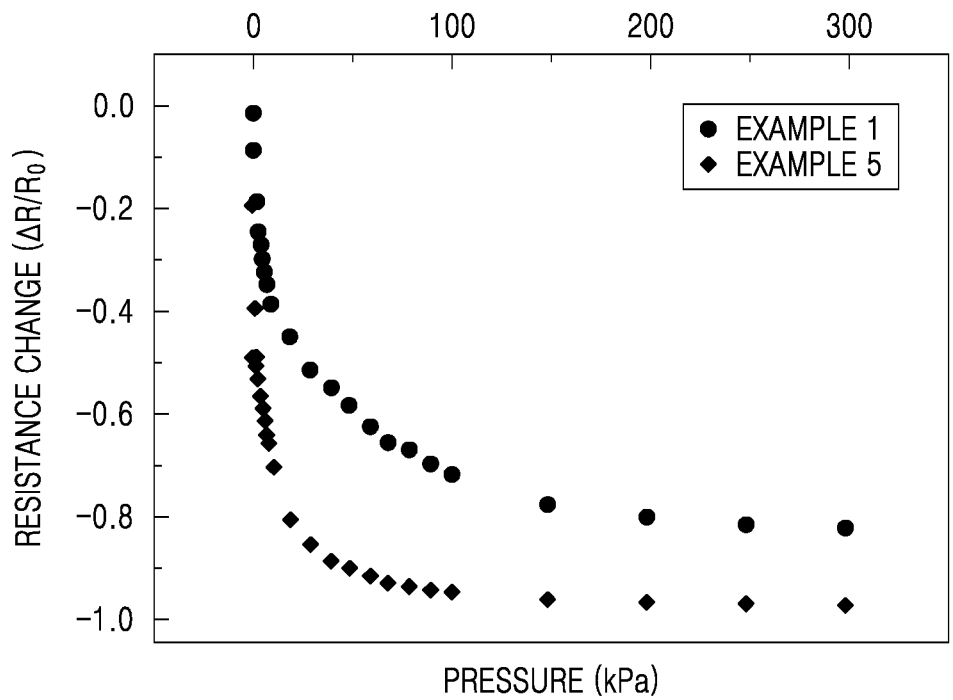
FIG. 10 is a graph showing a comparison of pressure-dependent resistance changes of the pressure sensors of Examples 1 and 5.

In addition, FIG. 10 is a graph showing a comparison of the pressure-dependent resistance changes of the pressure sensors of Examples 1 and 5. Referring to FIG. 10, it was confirmed that the pressure sensor in which the PDMS film of the second substrate had a pyramid structure exhibited excellent initial sensitivity and response as compared with the pressure sensor having the flat PDMS. However, in the absence of such a pyramid structure, it was confirmed that the pressure sensor exhibited excellent linearity with respect to the response. That is, when a pressure sensor was prepared by using a film having a pyramid structure or the like as the second substrate, the structure of the second substrate was able to cause a change in the contact resistance upon the pressure applied thereto, and in this regard, the response of the pressure sensor may be further improved as compared with a pressure sensor prepared by using a flat film of the second substrate.

Figure 11:
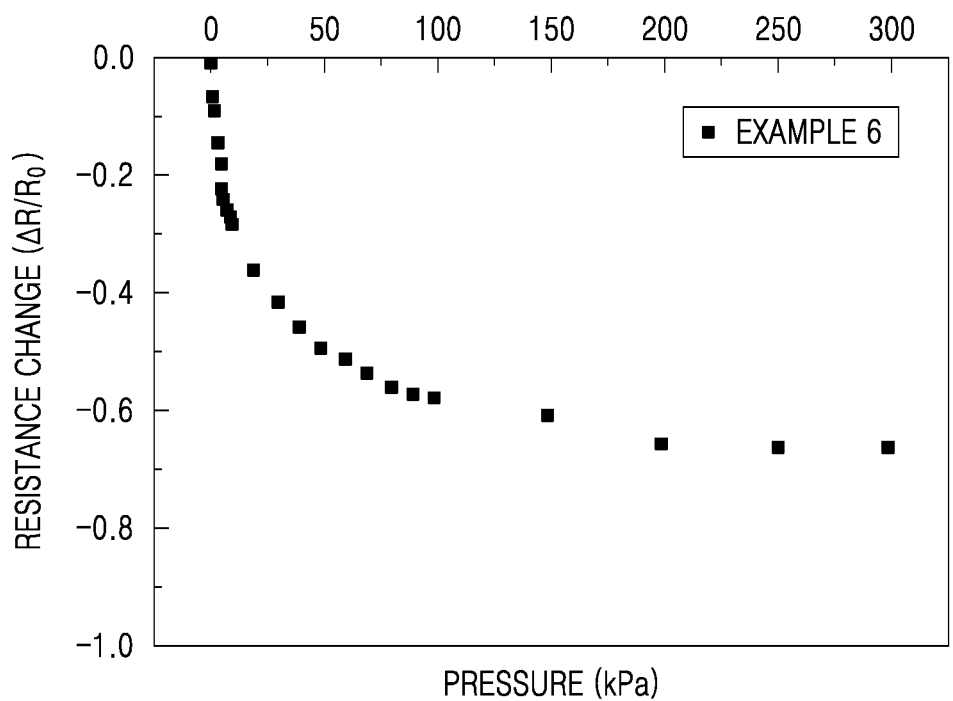
FIG. 11 is a graph showing resistance changes in a device including a pressure sensor prepared according to Example 6, measured when pressure is sequentially applied thereto from 0 kPa to 300 kPa.

Meanwhile, to confirm the effects of the addition of nanoparticles to the nanomesh film, changes in the resistance of the pressure sensor of Example 6 were measured by subsequently applying the pressure from 0 kPa to 300 kPa thereto, and the results are shown in FIG. 11. Referring to FIG. 11, it was confirmed that the nanomesh film including the nanoparticles also exhibited excellent response. That is, the nanomesh film including the nanoparticles may have a porous structure, resulting in improved recovery of the pressure sensor.

Figure 12:
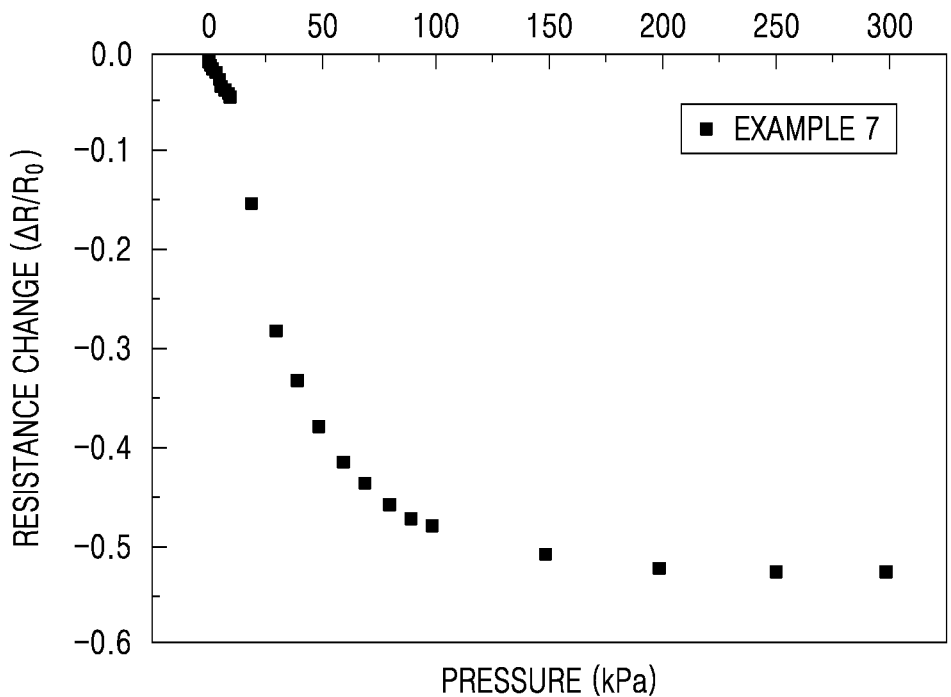
FIG. 12 is a graph showing resistance changes in a device including a pressure sensor prepared according to Example 7, measured when pressure is sequentially applied thereto from 0 kPa to 300 kPa.

Meanwhile, to confirm the driving property of the nanomesh film prepared by using a peptide, changes in the resistance of the pressure sensor of Example 7 were measured by subsequently applying the pressure from 0 kPa to 300 kPa thereto, and the results are shown in FIG. 12. Referring to FIG. 12, it was confirmed that the nanomesh film prepared by using a peptide also showed excellent response. Since a peptide is chemically synthesized and commercially available without a difficulty, the peptide may be used for the preparation of the nanomesh film in a simple process.

In addition, to verify whether use of a conductive material other than a nanomesh material may implement a pressure sensor operating on the same operation principle as the above, the pressure from 0 kP to 300 kPa was subsequently applied to the pressure sensor of Example 8, and changes in the resistance of the pressure sensor were measured. The results are shown in FIG. 13.

Figure 13:
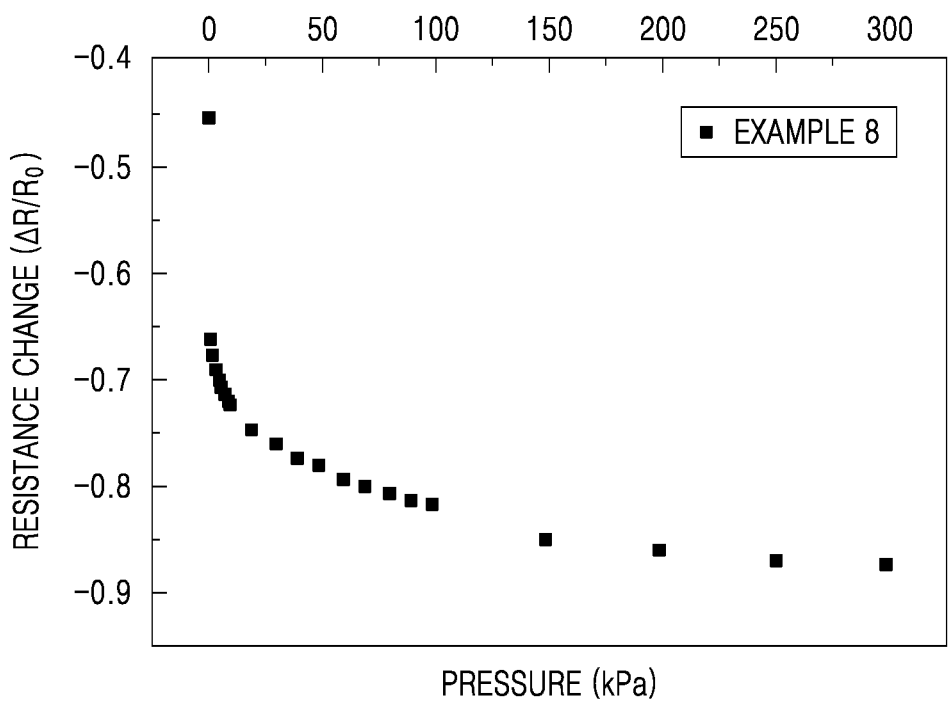
FIG. 13 is a graph showing resistance changes in a device including a pressure sensor prepared according to Example 8, measured when pressure is sequentially applied thereto from 0 kPa to 300 kPa.

Referring to FIG. 13, it was confirmed that use of a commercially available filter paper as a conductive material coated with carbon ink for the second layer of the present inventive concept was able to implement excellent characteristics of the pressure sensor.

Meanwhile, as described above, the discontinuous pattern of the conductive region may be not only a one-dimensional line pattern, but also a two-dimensional island-type pattern as shown in FIG. 14.

Figure 15:
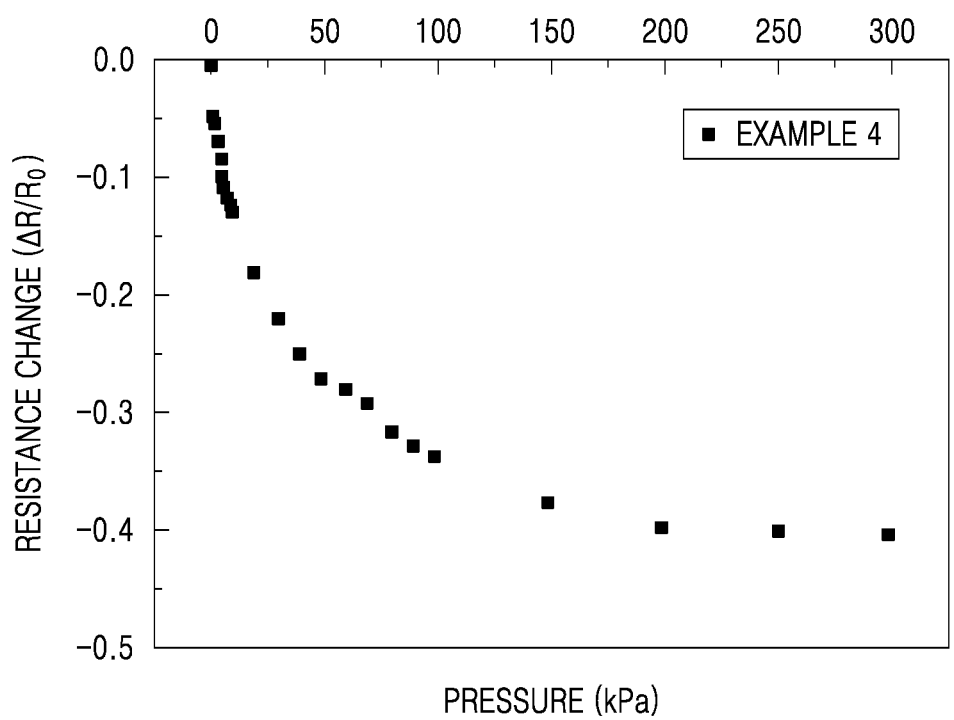
FIG. 15 a graph showing resistance changes in a device including a pressure sensor prepared according to Example 4, measured when pressure is sequentially applied thereto from 0 kPa to 300 kPa.

To determine the effects of the conductive region having such an island-type pattern disposed thereon, changes in the resistance of the pressure sensor of Example 4 were measured by subsequently applying the pressure from 0 kPa to 300 kPa thereto, and the results are shown in FIG. 15. Referring to FIG. 15, it was confirmed that, in the case of the conductive region including such an island-type pattern disposed thereon, a high-responsive pressure sensor was implemented.

In addition, in the case of the first substrate including the conductive region with an island-type pattern disposed thereon, as described above, the effect of determining not only the intensity of the pressure, but also the position to which the pressure was applied (i.e., the mapping effect) may be resulted based on the combination of the positions of the terminals at various positions According to an aspect of the present disclosure, there is provided a pressure-sensing apparatus capable of detecting an intensity of the pressure by using the pressure sensors 10, 20, and 30 of the present inventive concept.

Figure 16:
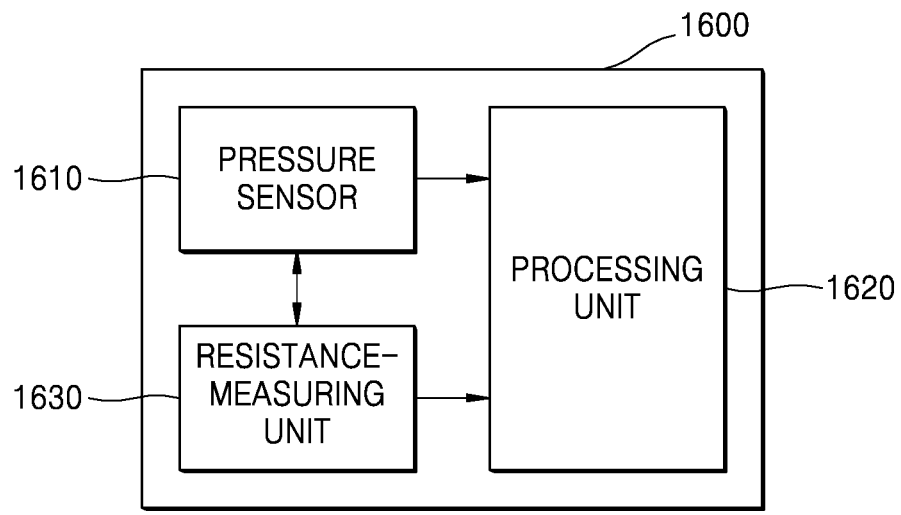
FIG. 16 is a block diagram showing a structure of a pressure-sensing apparatus 1600 according to an embodiment.

FIG. 16 is a block diagram showing a structure of a pressure-sensing apparatus 1600.

The pressure-sensing apparatus 1600 according to an embodiment includes, includes a pressure sensor 1610, a processing unit 1620, and a resistance-measuring unit 1630.

The pressure sensor 1610 may be, for example, the pressure sensor of FIG. 1, 2, or 14 as the pressure sensor 1610 according to the Examples above. The pressure sensor 1610 may include a first layer and a second layer, wherein the first layer includes a conductive region having first electrical conductivity and the second layer has second electrical conductivity Here, the first electrical conductivity may be the same as or greater than the second electrical conductivity, and the second layer may be disposed on the first layer. The pressure sensor 1610 may include a plurality of terminals. The plurality of the terminals may be electrically connected to the second layer, and spaced apart from the first layer. For example, as shown in FIGS. 1 and 2, the plurality of the terminals may be spaced apart from the first layer 131 or 231.

The resistance-measuring unit 1630 may measure resistance of the plurality of the terminals of the pressure sensor 1610. For example, the resistance-measuring unit 1630 may measure resistance of the plurality of the terminals by applying the pressure to the plurality of the terminals of the pressure sensor and subsequently measuring the current between the plurality of the terminals.

The processing unit 1620 may detect the intensity of the pressure based on the changed resistance value of the plurality of the terminals. The processing unit 1620 may control the resistance-measuring unit 1630 to measure the resistance value of the plurality of the terminal, and accordingly, an initial resistance value and a changed resistance value may be measured.

FIG. 17 is a diagram showing a process of measuring resistance between two terminals according to an embodiment.

The processing unit 1620 first measures initial resistance of the plurality of the terminals. The initial resistance may refer to resistance of the plurality of the terminals in the absence of pressure. For example, a resistance value with respect to a combination of resistance between terminals, such as resistance between a terminal 311 and a terminal 311*k*, resistance between a terminal 311*a* and a terminal 311*j*, resistance between a terminal 311*a* and a terminal 311*i*, resistance between a terminal 311 and a terminal 311*h*, or the like may be measured.

In addition, the processing unit 1620 may detect a changed resistance value by using the resistance-measuring unit 1630 after the initial resistance is measured.

To measure the resistance, the resistance-measuring unit 1630 may be used to apply a set voltage to each of the plurality of the terminals. For example, a high voltage may be applied to the terminal 311*a* using the resistance-measuring unit 1630. After applying a low voltage to the terminals 311*c*, 311*d*, 311*e*, 311*f*, 311*g*, 311*h*, 311*i*, 311*j*, and 311*k*, the current flowing between the terminal 311*a* and the other remaining terminals may e measure so as to measure a resistance value therebetween.

When the changed resistance value is detected, the processing unit 1620 determines the intensity of the pressure based on the detected changed resistance value. For example, by comparing the changed resistance value with the predetermined standard value, it is determined by the processing unit 1620 that the pressure is applied if the changed resistance value is greater than the standard value. In addition, based on the magnitude of the changed resistance value, the processing unit 1620 may determine the intensity of the pressure. For example, the processing unit 1620 may determine the intensity of the pressure based on the changed resistance value using a look-up table, a conversion equation, or the like.

In an embodiment, the conductive region included in the first layer may have a one-dimensional array as shown in FIG. 2. Here, the processing unit 1620 may measure the intensity of the pressure by using the one-dimensionally arrayed pressure sensor.

In one or more embodiments, the conductive region included in the first layer may have a two-dimensional array as shown in FIG. 14. Here, the processing unit 1620) may measure the intensity of the pressure and the position to which the pressure is applied, based on the changed resistance value between the plurality of the terminals. The processing unit 1620 may also determine the position of electrodes whose changed resistance value exceeds the reference value, and the position to which the pressure is applied based on the changed resistance value of the corresponding electrodes. In addition, the processing unit 1620 may determine the intensity of the pressure based on the changed resistance value.

In an embodiment, the conductive region included in the first layer may have different electrical conductivity. For example, the conductive region included in the first layer may have different electrical conductivity depending on a position. Even if the conductive region included in the first layer has different electrical conductivity, the electrical conductivity of the conductive region included in the first layer is the same as or greater than that of the second layer. In an embodiment, as the number of cases of the changed resistance value upon the position to which the pressure is applied, the position to which the pressure is applied and the intensity of the pressure may be further effectively and accurately detected.

Figure 18:
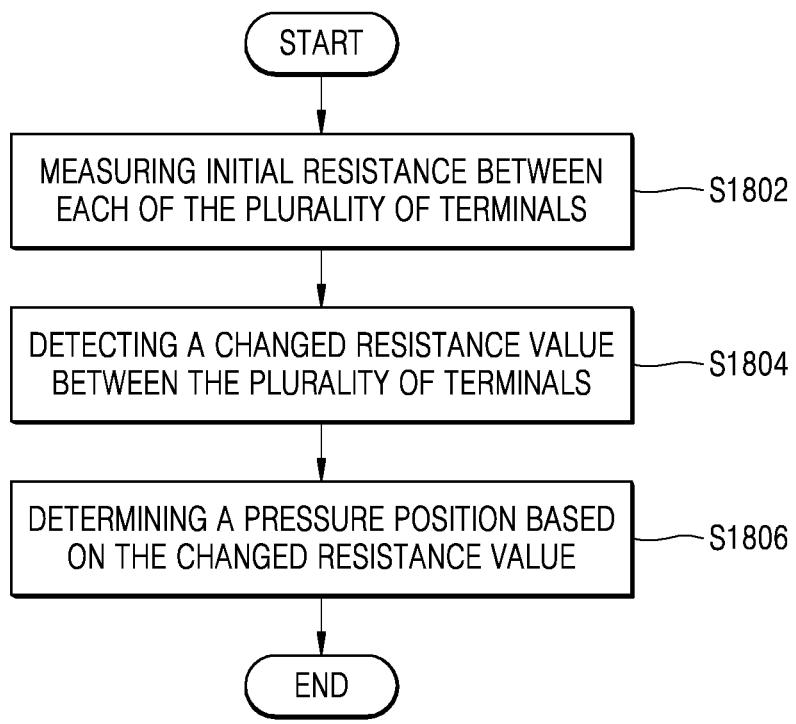
FIG. 18 is a flow chart describing a process of sensing pressure according to an embodiment.

FIG. 18 is a flow chart describing a process of sensing pressure according to an embodiment.

In the process of sensing the pressure according to an embodiment, the pressure sensor of the Examples above was used and implemented by various devices including the processing unit. In the present specification of the inventive concept, Examples regarding the process of sensing the pressure using a pressure-sensing apparatus 1600 of FIG. 16 are provided in detail First, the pressure-sensing apparatus was to measure an initial resistance of the plurality of the terminals (S1802).

Next, the changed resistance value in the plurality of the terminals was detected by the pressure-sensing apparatus (S1804). To measure a changed resistance value after the initial resistance was measured, the pressure-sensing apparatus was able to measure resistance values of the plurality of the terminals by applying the voltage to the plurality of the terminals and subsequently measuring the current thereof.

Next, the pressure-sensing apparatus may determine the intensity of the pressure based on the changed resistance value of the plurality of the terminals (S1806). In an embodiment where the first layer had a two-dimensional conductive region array, the pressure-sensing apparatus may determine the position to which the pressure was applied based on the combination of the terminals of which the changed resistance value was greater than the standard value of the terminals.

According to the one or more embodiments, a pressure sensor uses a typical conductive material, but is able to easily detect a change in the resistance upon the application of the pressure. Accordingly, the pressure sensor may have excellent sensitivity and mapping effects, and in this regard, an intensity of the pressure applied to the pressure sensor and a position to which the pressure is applied are determined.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A pressure sensor comprising:
a first layer comprising at least one conductive region having first electrical conductivity;
a second layer contacting the first layer to be disposed thereon and having second electrical conductivity; and
a plurality of terminals directly electrically connected to the second layer and spaced apart from and disposed outside the at least one conductive region,
wherein electrical conductivity of the at least one conductive region is the same as or greater than that of the second layer, and
wherein the at least one conductive region has a discontinuous pattern internally and is not directly but through the second layer electrically connected to the plurality of terminals.

2. The pressure sensor of claim 1, wherein resistance of the first layer (first layer resistance, $R_1$), resistance of the second layer (second layer resistance, $R_2$), and resistance between the first layer and the second layer (contact resistance, $R_{1-2}$) has a relationship of $R_1 \leq R_2 < R_{1-2}$ before application of external pressure.

3. The pressure sensor of claim 1, wherein an electric current changes depending on application of pressure.

4. The pressure sensor of claim 1, wherein the at least one conductive region has a line pattern disposed discontinuously in one direction or an island-type pattern disposed discontinuously in a plurality of directions.

5. The pressure sensor of claim 1, wherein the discontinuous pattern has a rectangular, triangular, polygonal, circular, elliptical, stripe, or irregular shape, or a combination thereof.

6. The pressure sensor of claim 1, wherein the discontinuous pattern has the same or different electrical conductivity.

7. The pressure sensor of claim 1, wherein the first layer is disposed on a first substrate, and
the sum of areas of the at least one conductive region is in a range of about 25% to about 95% based on the total area of the first substrate.

8. The pressure sensor of claim 1, wherein the first layer and the second layer each independently comprises at least one selected from gold (Au), silver (Ag), copper (Cu), aluminum (Al), platinum (Pt), zinc (Zn), nickel (Ni), an alloy or composite thereof, a conductive polymer, a conductive fiber, and a graphitic material.

9. The pressure sensor of claim 1, wherein at least one of the first layer and the second layer includes at least one selected from a graphene sheet, a highly oriented pyrolytic graphite (HOPG) sheet, a graphene oxide sheet, a reduced graphene oxide sheet, a single-walled carbon nanotube, a double-walled carbon nanotube, a multi-walled carbon nanotube, fullerene, and a composite thereof.

10. The pressure sensor of claim 8, wherein the second layer comprises the graphitic material, and further comprises a phage binding to the graphitic material, wherein the phage binding is between the graphitic material and a peptide displayed on a coat protein of the phage or a fragment thereof.

11. The pressure sensor of claim 8, wherein the second layer comprises the graphitic material and a peptide binding to the graphitic material.

12. The pressure sensor of claim 1, wherein an internal structure of the second layer is a network structure.

13. The pressure sensor of claim 12, wherein the network structure further comprises a nanoparticle.

14. The pressure sensor of claim 1, further comprising:
a first substrate disposed on the first layer; and
a second substrate disposed on a surface of the second layer not facing the first substrate.

15. The pressure sensor of claim 14, wherein at least one of the first substrate and the second substrate has an uneven structure including a convex portion, a concave portion, or a combination thereof.

16. The pressure sensor of claim 15, wherein a cross section of the convex portion or the concave portion has a triangular, square, polygonal, circular, oval, or irregular shape.

17. The pressure sensor of claim 14, wherein the first substrate, the second substrate, or both first and second substrates are each a flexible substrate.

18. A device comprising the pressure sensor of claim 1.

19. A method of sensing pressure by using a pressure sensor comprising a first layer having first electrical conductivity, a second layer having second electrical conductivity, and a plurality of terminals directly electrically connected to the second layer, the method comprising:
measuring initial resistance between each of the plurality of terminals;
detecting a changed resistance value between each of the plurality of terminals; and
determining a pressure intensity based on the changed resistance value between each of the plurality of terminals,
wherein the first layer comprises at least one conductive region having the first electrical conductivity and a discontinuous pattern internally, and
the plurality of terminals is spaced apart from and disposed outside the at least one conductive region, and not directly but through the second layer electrically connected to the at least one conductive region.

20. The method of claim 19, wherein
the second layer contacts the first layer to be disposed thereon.

21. The method of claim 19, wherein the first electrical conductivity is the same as or greater than the second electrical conductivity.

22. The method of claim 20, wherein the at least one conductive region comprises a conductive region array of n*m (where n and m are each independently a natural number of 1 or more),
the plurality of terminals comprise, outside the conductive region array, a plurality of electrodes disposed in a horizontal direction and a plurality of electrodes disposed in a vertical direction, and the method further comprises determining a pressure intensity and a pressure position to which the pressure is applied based on the changed resistance value between each of the plurality of terminals.

23. The method of claim 22, wherein the determining of the pressure position comprises determining a pressure position by a combination of terminals whose changed resistance value is greater than a standard resistance value.

24. The method of claim 22, wherein the conductive region array comprises conductive regions having different electrical conductivity each other.

25. A pressure-sensing apparatus comprising:
a pressure sensor comprising a first layer having first electrical conductivity, a second layer having second electrical conductivity, and a plurality of terminals directly electrically connected to the second layer;
a resistance-measuring unit measuring resistance between each of the plurality of terminals; and
a processing unit measuring initial resistance between each of the plurality of terminals and detecting a changed resistance value between each of the plurality of terminals and determining a pressure intensity based on the changed resistance value between each of the plurality of terminals,
wherein the first layer comprises at least one conductive region having the first electrical conductivity and a discontinuous pattern internally, and
the plurality of terminals is spaced apart from and disposed outside the at least one conductive region, and not directly but through the second layer electrically connected to the at least one conductive region.

26. The pressure-sensing apparatus of claim 25, wherein the second layer contacts the first layer to be disposed thereon.

27. The pressure-sensing apparatus of claim 25, wherein the first electrical conductivity is the same as or greater than the second electrical conductivity.

28. The pressure-sensing apparatus of claim 26, wherein the at least one conductive region comprises a conductive region array of n*m (where n and m are each independently a natural number of 1 or more),
the plurality of terminals comprise, outside the conductive region array, a plurality of electrodes disposed in a horizontal direction and a plurality of electrodes disposed in a vertical direction, and
the processing unit determines a pressure intensity and a pressure position to which the pressure is applied, based on a changed resistance value between each of the plurality of electrodes.

29. The pressure-sensing apparatus of claim 28, wherein the processing unit determines a pressure position by a combination of terminals whose changed resistance value is greater than a standard resistance value.

30. The pressure-sensing apparatus of claim 28, wherein the conductive region array comprises conductive regions having different electrical conductivity each other.

31. A pressure sensor comprising:
a first layer comprising at least one conductive region having first electrical conductivity;
a second layer contacting the first layer to be disposed thereon and having second electrical conductivity; and
a plurality of terminals directly electrically connected to the second layer, not directly but through the second layer electrically connected to the at least one conductive region, and spaced apart from and disposed outside the at least one conductive region,
wherein the first layer comprises the plurality of terminals, and
wherein electrical conductivity of the at least one conductive region is the same as or greater than that of the second layer.

32. A method of sensing pressure by using a pressure sensor comprising a first layer having first electrical conductivity, a second layer having second electrical conductivity, and a plurality of terminals directly electrically connected to the second layer, the method comprising:
measuring initial resistance between each of the plurality of terminals;
detecting a changed resistance value between each of the plurality of terminals; and
determining a pressure intensity based on the changed resistance value between each of the plurality of terminals,
wherein the plurality of terminals is spaced apart from and disposed outside the first layer, and not directly but through the second layer electrically connected to the first layer.

33. A pressure-sensing apparatus comprising:
a pressure sensor comprising a first layer including at least one conductive region having first electrical conductivity, a second layer having second electrical conductivity, and a plurality of terminals directly electrically connected to the second layer;
a resistance-measuring unit measuring resistance between each of the plurality of terminals; and
a processing unit measuring initial resistance between each of the plurality of terminals, detecting a changed resistance value between each of the plurality of terminals, and determining a pressure intensity based on the changed resistance value between each of the plurality of terminals,
wherein the plurality of terminals is spaced apart from and disposed outside the at least one conductive region, and not directly but through the second layer electrically connected to the at least one conductive region.

* * * * *

SEQUENCE LISTING

```
<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is W, Y, F or H
<220> FEATURE:
<221> NAME/KEY: VARIANT
<222> LOCATION: (6)..(6)
<223> OTHER INFORMATION: X is D, E, N or Q
<220> FEATURE:
<221> NAME/KEY: VARIANT
<222> LOCATION: (7)..(7)
<223> OTHER INFORMATION: X is I, L, or V

<400> SEQUENCE: 1

Xaa Ser Xaa Ala Ala Xaa Xaa Pro
1               5

<210> SEQ ID NO 2
<211> LENGTH: 8
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (2)..(2)
<223> OTHER INFORMATION: X is D, E, N, or Q
<220> FEATURE:
<221> NAME/KEY: VARIANT
<222> LOCATION: (4)..(4)
<223> OTHER INFORMATION: X is I, L, or V
<220> FEATURE:
<221> NAME/KEY: VARIANT
<222> LOCATION: (5)..(5)
<223> OTHER INFORMATION: X is D, E, N, or Q
<220> FEATURE:
<221> NAME/KEY: VARIANT
<222> LOCATION: (7)..(7)
<223> OTHER INFORMATION: X is I, L, or V

<400> SEQUENCE: 2

Xaa Xaa Pro Xaa Xaa Ala Xaa Pro
1               5
```

<210> SEQ ID NO 3
<211> LENGTH: 7
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (2)..(2)
<223> OTHER INFORMATION: X is W, Y, F, or H
<220> FEATURE:
<221> NAME/KEY: VARIANT
<222> LOCATION: (5)..(5)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 3

Ser Xaa Ala Ala Xaa Xaa Pro
1               5

<210> SEQ ID NO 4
<211> LENGTH: 7
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is I, L, or V
<220> FEATURE:
<221> NAME/KEY: VARIANT
<222> LOCATION: (4)..(4)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 4

Xaa Pro Xaa Xaa Ala Xaa Pro
1               5

<210> SEQ ID NO 5
<211> LENGTH: 7
<212> TYPE: PRT
<213> ORGANISM: Artificial Sequence
<220> FEATURE:
<223> OTHER INFORMATION: peptide selectively binding to graphitic
      materials

<400> SEQUENCE: 5

Ser Trp Ala Ala Asp Ile Pro
1               5

<210> SEQ ID NO 6
<211> LENGTH: 7
<212> TYPE: PRT
<213> ORGANISM: Artificial Sequence
<220> FEATURE:
<223> OTHER INFORMATION: peptide selectively binding to graphitic
      materials -continued

<400> SEQUENCE: 6

Asn Pro Ile Gln Ala Val Pro
1               5

<210> SEQ ID NO 7
<211> LENGTH: 41
<212> TYPE: DNA
<213> ORGANISM: Artificial Sequence
<220> FEATURE:
<223> OTHER INFORMATION: BamH I_SM_upper which is a primer used for
      site-directed mutation

<400> SEQUENCE: 7
aaggccgctt ttgcgggatc ctcaccctca gcagcgaaag a                    41

<210> SEQ ID NO 8
<211> LENGTH: 40
<212> TYPE: DNA
<213> ORGANISM: Artificial Sequence
<220> FEATURE:
<223> OTHER INFORMATION: BamH I_SM_lower which is a primer used for
      site-directed mutation

<400> SEQUENCE: 8
ctttcgctgc tgagggtgag gatcccgcaa aagcggcctt                      40

<210> SEQ ID NO 9
<211> LENGTH: 90
<212> TYPE: DNA
<213> ORGANISM: Artificial Sequence
<220> FEATURE:
<223> OTHER INFORMATION: BamM13HK_P8_primer which is an extension primer
      used for preparation

<400> SEQUENCE: 9
ttaatggaaa cttcctcatg aaaaagtctt tagtcctcaa agcctctgta gccgttgcta    60
ccctcgttcc gatgctgtct ttcgctgctg                                    90

<210> SEQ ID NO 10
<211> LENGTH: 95
<212> TYPE: DNA
<213> ORGANISM: Artificial Sequence
<220> FEATURE:
<223> OTHER INFORMATION: M13HK_P8 which is a library oligonucleotide
      used for preparation
<220> FEATURE:
<221> NAME/KEY: misc_feature
<222> LOCATION: (1)..(95)
<223> OTHER INFORMATION: n is a, g, c or t
<220> FEATURE:
<221> NAME/KEY: misc_feature
<222> LOCATION: (1)..(95)
<223> OTHER INFORMATION: m is a or c

<400> SEQUENCE: 10
aaggccgctt ttgcgggatc cnnmnnmnnm nnmnnmnnmn nmncagcagc gaaagacagc    60
atcggaacga gggtagcaac ggctacagag gcttt                              95

<210> SEQ ID NO 11
<211> LENGTH: 27
<212> TYPE: PRT
<213> ORGANISM: artificial sequence
<220> FEATURE:
<223> OTHER INFORMATION: synthetic peptide construct

<400> SEQUENCE: 11

```
Ala Asp Ser Trp Ala Ala Asp Ile Pro Asp Pro Ala Gly Gly Gly Ala
1               5               10                  15

Asp Ser Trp Ala Ala Asp Ile Pro Asp Pro Ala
            20              25
```